(12) United States Patent
Assell et al.

(10) Patent No.: US 7,632,274 B2
(45) Date of Patent: Dec. 15, 2009

(54) THIN CUTTER BLADES WITH RETAINING FILM FOR PREPARING INTERVERTEBRAL DISC SPACES

(75) Inventors: Robert L. Assell, Wilmington, NC (US); T. Matthew Womble, Leland, NC (US); Eugene A. Dickhudt, Lino Lakes, MN (US)

(73) Assignee: TranS1 Inc., Wilmington, NC (US)

( * ) Notice: Subject to any disclaimer, the term of this patent is extended or adjusted under 35 U.S.C. 154(b) by 0 days.

(21) Appl. No.: 11/712,241

(22) Filed: Feb. 28, 2007

(65) Prior Publication Data

US 2007/0265652 A1    Nov. 15, 2007

(51) Int. Cl.
*A61B 17/00* (2006.01)

(52) U.S. Cl. ....................................................... 606/79

(58) Field of Classification Search .................... 30/351, 30/353, 356; 83/663; 407/29.1, 29.14, 29.15, 407/53; 606/79–85, 86 R, 180–182
See application file for complete search history.

(56) References Cited

U.S. PATENT DOCUMENTS

| | | | |
|---|---|---|---|
| 1,092,914 A | 4/1914 | Jones | |
| 1,388,547 A | 8/1921 | Burns | |
| 1,638,807 A * | 8/1927 | Hopwood | 30/318 |
| 2,513,663 A * | 7/1950 | McDaniel | 30/318 |
| 2,730,101 A * | 1/1956 | Hoffman | 606/159 |
| 3,367,326 A | 2/1968 | Frazier et al. | |
| 3,670,732 A | 6/1972 | Robinson | |
| 4,046,144 A | 9/1977 | McFarlane | |
| 5,030,201 A * | 7/1991 | Palestrant | 604/22 |
| 5,231,910 A | 8/1993 | Harsch et al. | |
| 5,376,094 A | 12/1994 | Kline | |
| 5,376,100 A * | 12/1994 | Lefebvre | 606/180 |
| 5,591,170 A | 1/1997 | Spievack et al. | |
| 5,693,011 A * | 12/1997 | Onik | 604/22 |
| 5,709,697 A * | 1/1998 | Ratcliff et al. | 606/180 |
| 5,787,591 A | 8/1998 | Lu | 30/355 |
| 5,928,239 A | 7/1999 | Mirza | |
| 5,935,143 A | 8/1999 | Hood | 606/169 |
| 5,937,524 A | 8/1999 | Hornsby | |
| 5,979,056 A | 11/1999 | Andrews | |
| 6,159,179 A | 12/2000 | Simonson | |
| 6,383,188 B2 | 5/2002 | Kuslich et al. | |
| 6,389,699 B1 * | 5/2002 | Ecer | 30/346.54 |
| 6,440,138 B1 | 8/2002 | Reiley et al. | |
| 6,574,868 B1 | 6/2003 | Overholt | 30/155 |
| 6,740,090 B1 * | 5/2004 | Cragg et al. | 606/79 |
| 6,746,451 B2 | 6/2004 | Middleton et al. | |

(Continued)

*Primary Examiner*—Thomas C Barrett
*Assistant Examiner*—Nicholas Woodall
(74) *Attorney, Agent, or Firm*—The Eclipse Group LLP; Kevin E. Flynn

(57) ABSTRACT

Cutter blades made of shape memory materials. Rotation of a cutter blade as part of a cutter assembly within an intervertebral disc space cuts the material present there for removal from the intervertebral disc space. Cutter blades with different attributes (such as throw length, cutter blade angle, type and location of blade edges) are adapted to achieve different objectives within the intervertebral disc space. The use of a hollow ground to enhance the cutting action of a blade edge is described in connection with the creation of cutter blades. A variety of thin cutter blades are described which may be used in the interior of a thin intervertebral disc (having a reduced distance between the endplates of the adjacent vertebral bodies).

17 Claims, 23 Drawing Sheets

U.S. PATENT DOCUMENTS

| | | |
|---|---|---|
| 2002/0016604 A1 | 2/2002 | Boock et al. ................. 606/159 |
| 2002/0188299 A1 | 12/2002 | Reiley et al. |
| 2003/0205024 A1 | 11/2003 | Pelton ....................... 52/786.1 |
| 2004/0215343 A1 | 10/2004 | Hochschuler et al. |
| 2005/0113836 A1* | 5/2005 | Lozier et al. ................. 606/80 |
| 2005/0165406 A1 | 7/2005 | Assell et al. ................... 606/86 |
| 2005/0228420 A1 | 10/2005 | Harding et al. ............. 606/167 |
| 2005/0230510 A1 | 10/2005 | Flanhardt et al. ............ 241/242 |
| 2005/0257660 A1 | 11/2005 | Hayden ....................... 83/846 |
| 2006/0241629 A1* | 10/2006 | Krebs et al. ................... 606/80 |

* cited by examiner

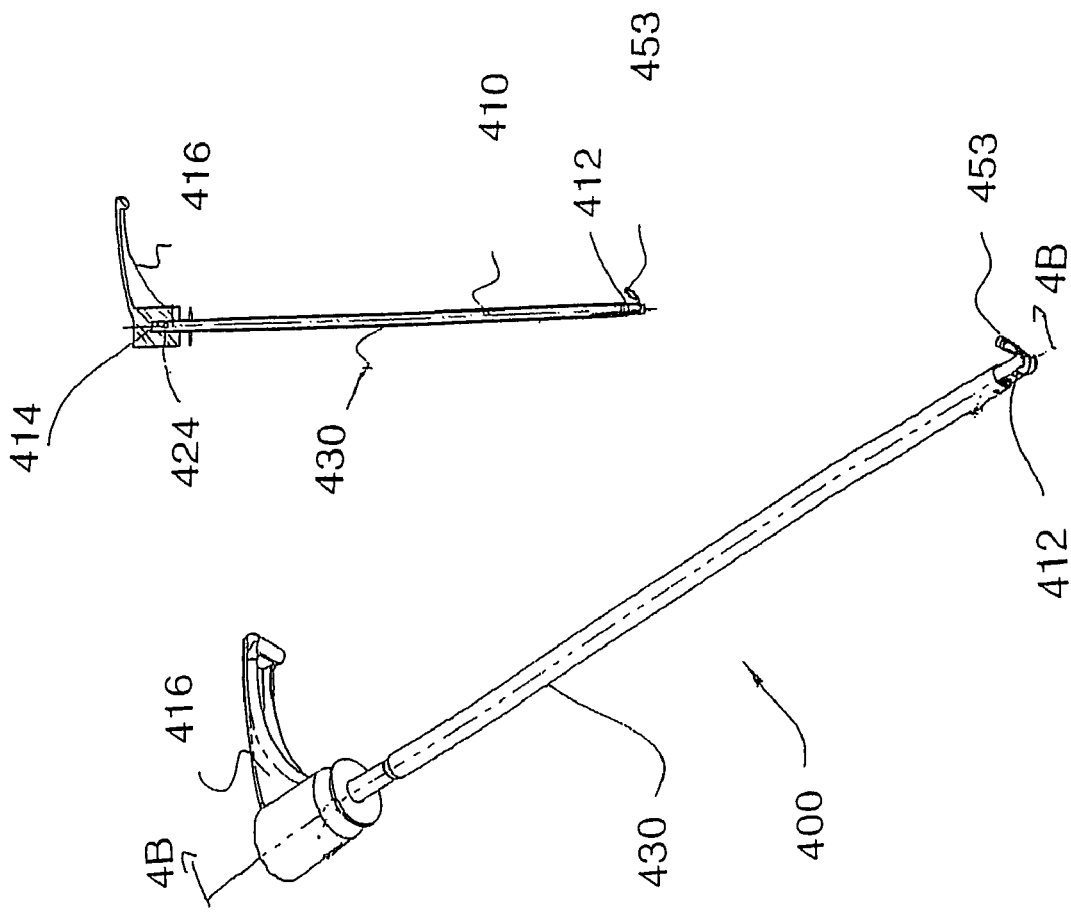

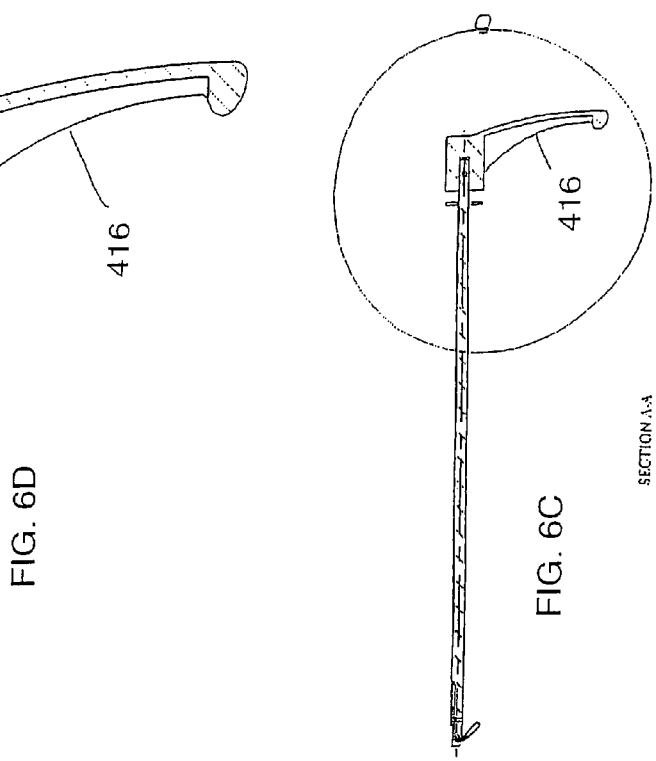
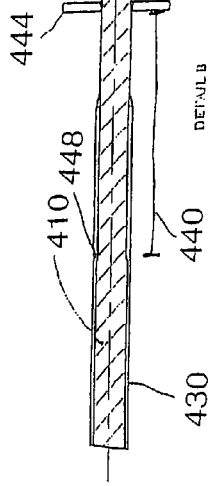
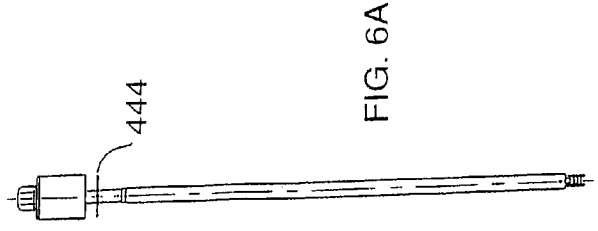
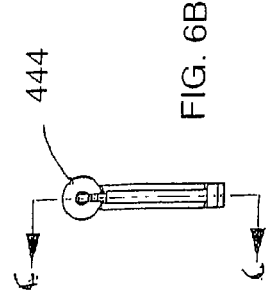
FIG. 6D
FIG. 6C
FIG. 6A
FIG. 6B

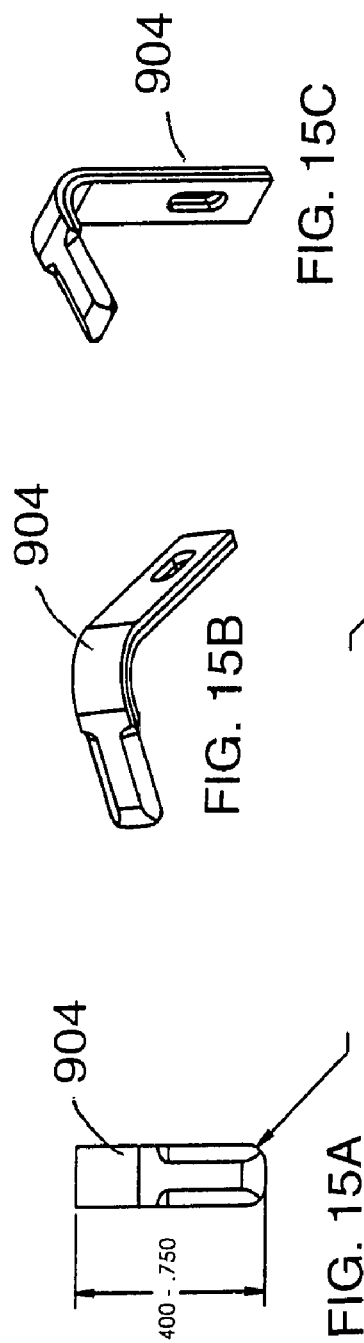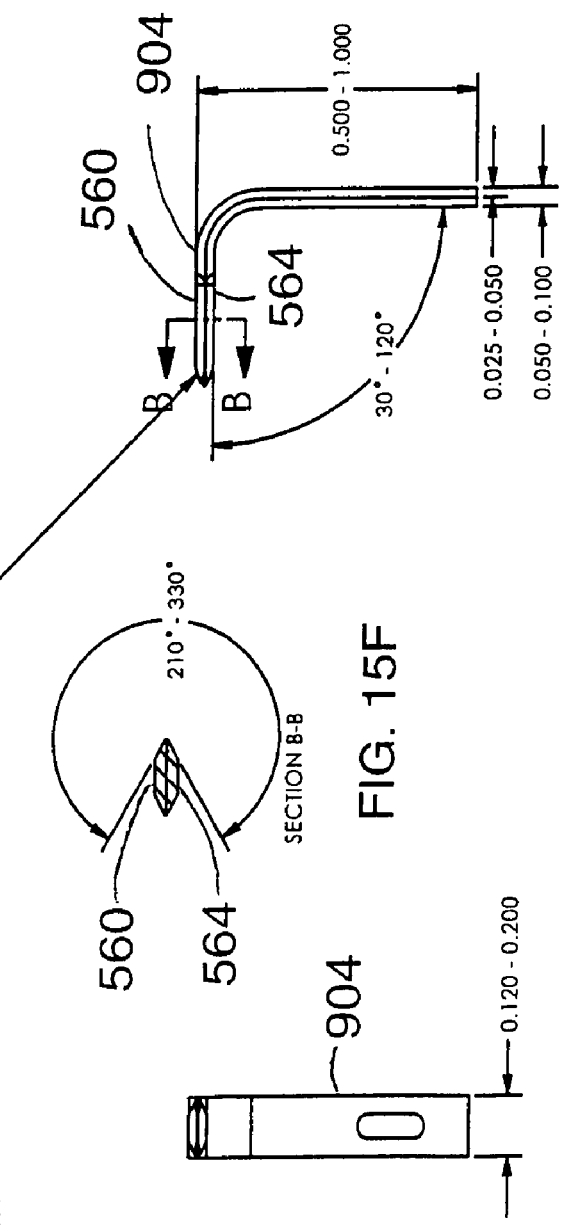

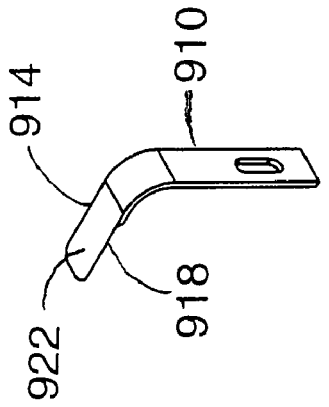
FIG. 16C
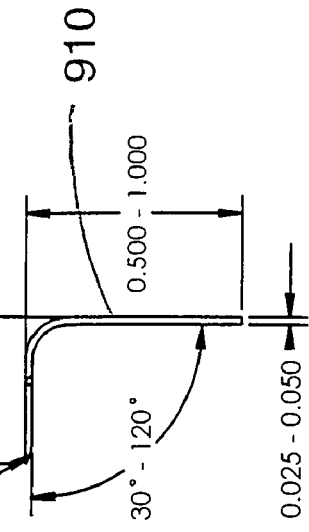
FIG. 16F
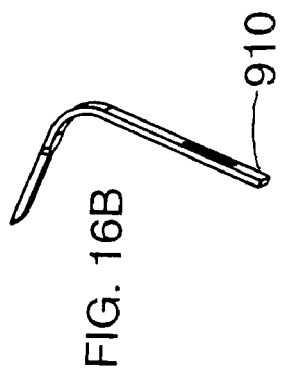
FIG. 16B
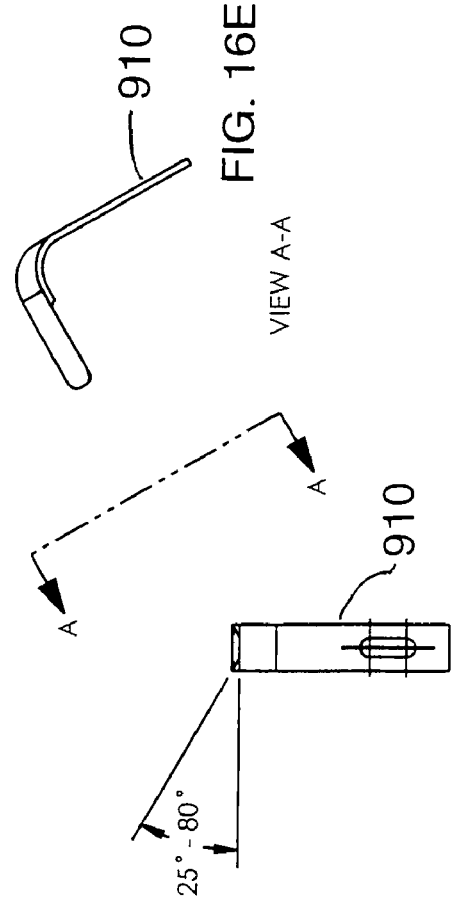
FIG. 16E
VIEW A-A
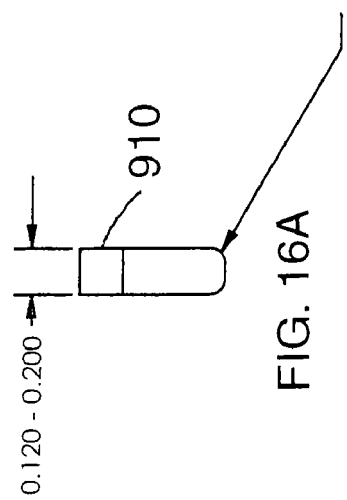
FIG. 16A
FIG. 16D

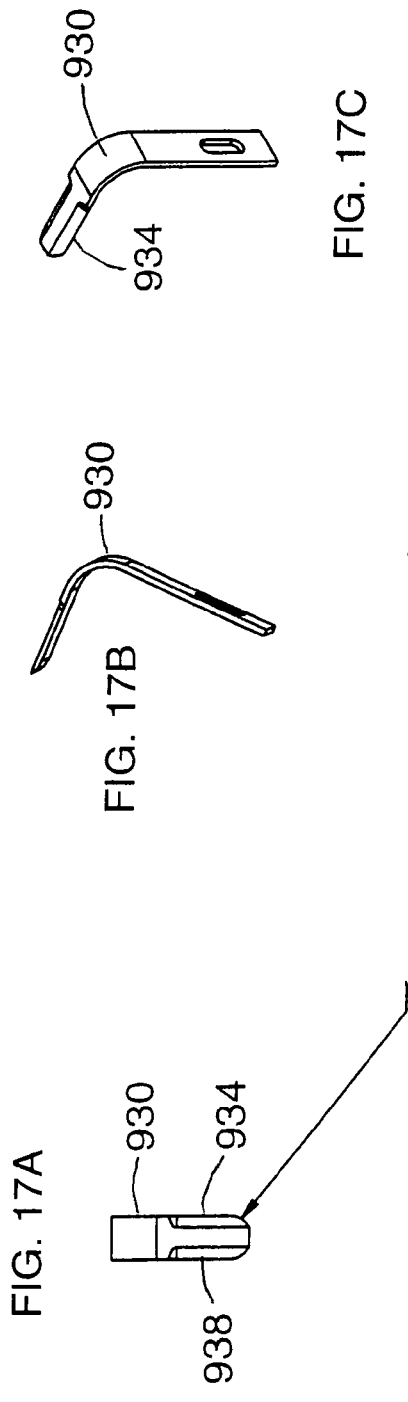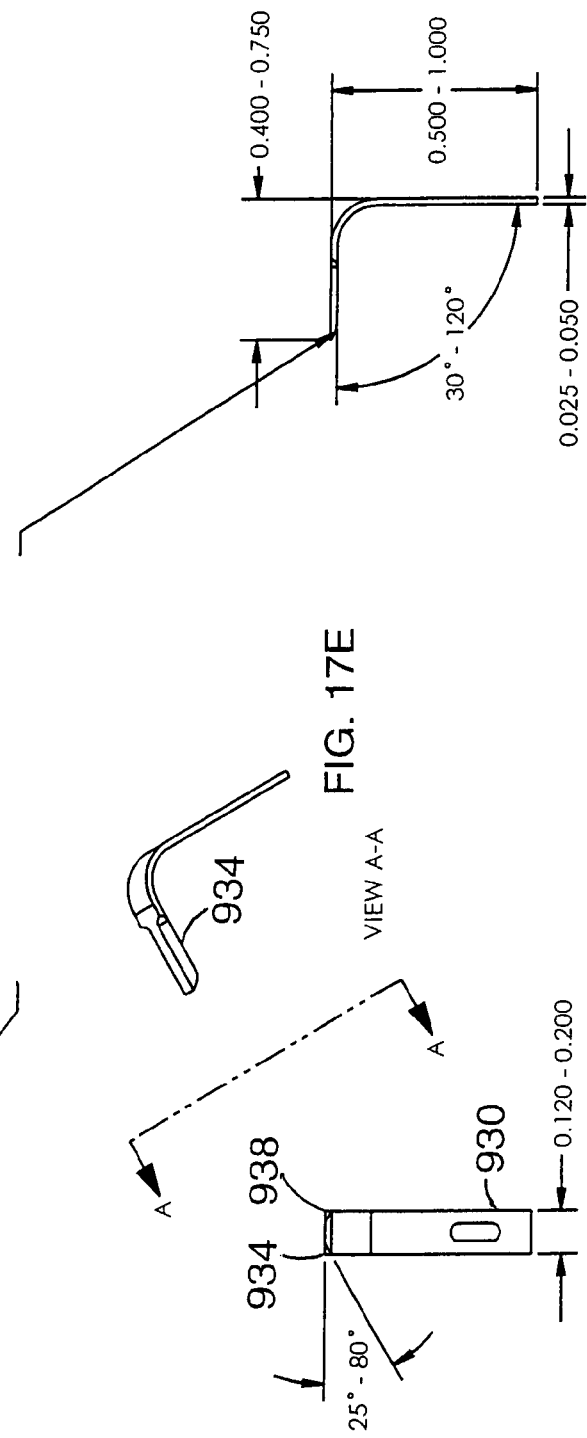

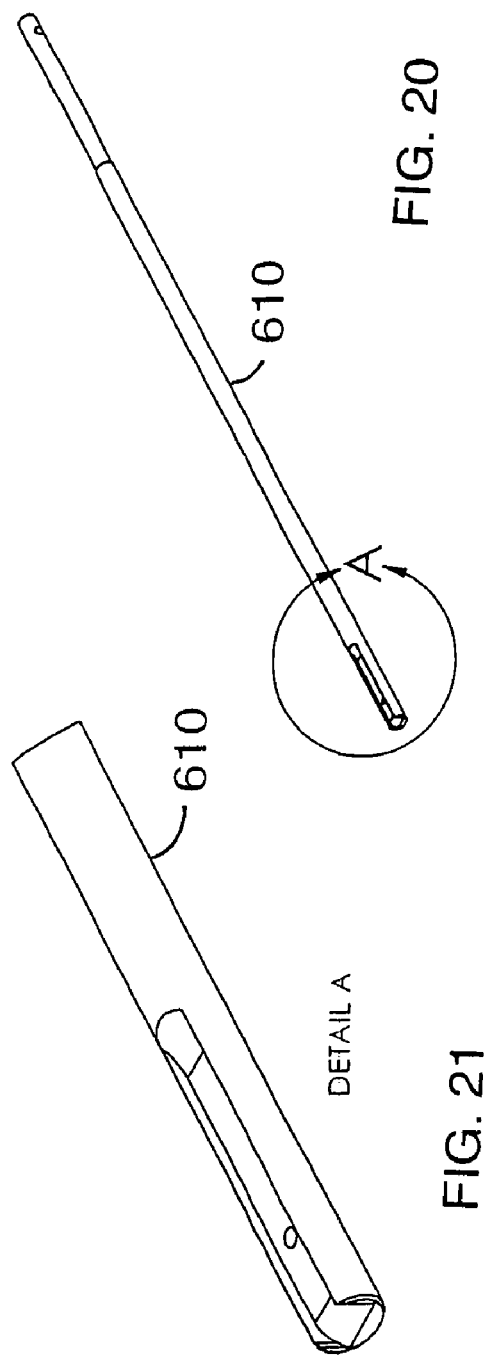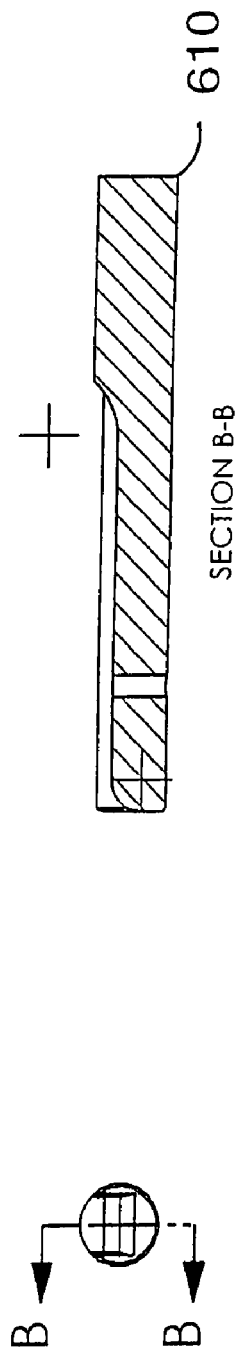

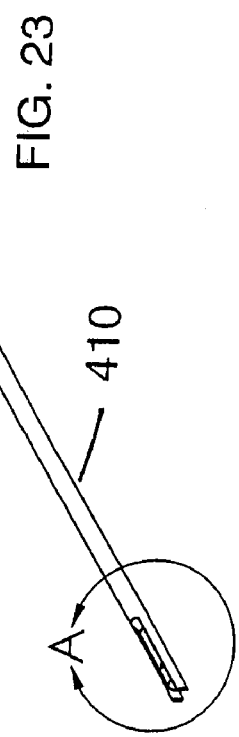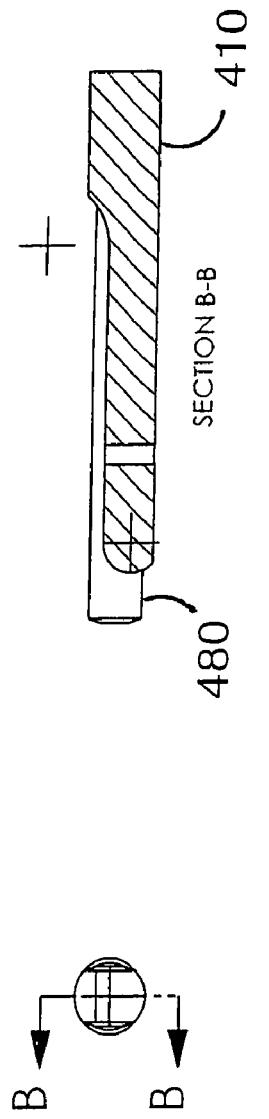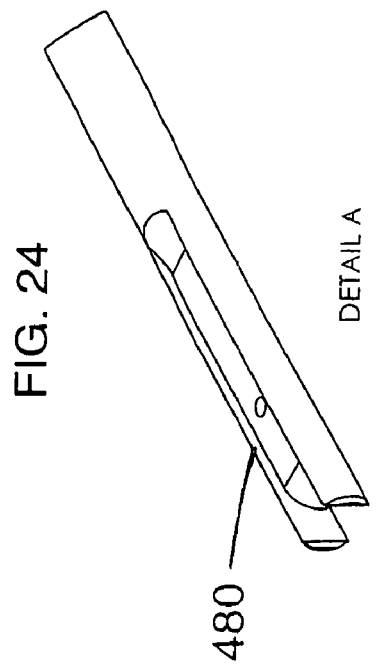
FIG. 23
FIG. 25
FIG. 24

THIN CUTTER BLADES WITH RETAINING FILM FOR PREPARING INTERVERTEBRAL DISC SPACES

This application builds upon a series of applications filed on behalf of assignee. In particular this application extends the innovative work in the area of manipulating material in the spine described in co-pending and commonly assigned U.S. patent application Ser. No. 10/972,077 for Method and Apparatus for Manipulating Material in the Spine filed Oct. 22, 2004 and subsequently published as United States Patent Application No. US 2005/0149034 A1 and U.S. Provisional Patent Application No. 60/778,035 for Method and Apparatus for Tissue Manipulation and Extraction filed Feb. 28, 2006. This application claims priority to the '035 and incorporates in their entirety by reference both the '077 application and the '035 application. This application incorporates by reference various applications claimed as priority documents by the '077 application specifically: U.S. Provisional Patent Application No. 60/513,899, filed on Oct. 23, 2003, and U.S. patent application Ser. No. 10/309,416, filed on Dec. 3, 2002 (now U.S. Pat. No. 6,921,403), which is a continuation-in-part of U.S. patent application Ser. No. 10/125,771, filed on Apr. 18, 2002 (now U.S. Pat. No. 6,899,716), which is a continuation-in-part of U.S. patent application Ser. No. 09/848,556, filed on May 3, 2001, (now U.S. Pat. No. 7,014,633) which is a continuation-in-part of U.S. patent application Ser. No. 09/782,583, filed on Feb. 13, 2001 (now U.S. Pat. No. 6,558,390), which claims priority to U.S. Provisional Patent Application No. 60/182,748, filed on Feb. 16, 2000. U.S. patent application Ser. No. 09/782,534 teaches various types of techniques for using cutting tools for removing disc material and preparation of spinal treatment sites that comprise a spinal disc, for example, a method of removing at least a portion of the nucleus through an anterior tract axial bore while leaving the annulus fibrosus intact.

This application extends the innovative work in the area of spinal motion preservation assemblies described in co-pending and commonly assigned U.S. patent application Ser. No. 11/586,338 for Spinal Motion Preservation Assemblies filed Oct. 24, 2006 and U.S. patent application Ser. No. 11/586,486 for Methods and Tools for Delivery of Spinal Motion Preservation Assemblies filed Oct. 24, 2006. This application incorporates by reference both '338 and the '486 application.

The '338 application claims priority to U.S. patent application Ser. No. 11/256,810 for Spinal Motion Preservation Assemblies and U.S. patent application Ser. No. 11/259,614 Driver Assembly for Simultaneous Axial Delivery of Spinal Implants. This application incorporates by reference both the '810 application and the '614 application. This application incorporates by reference two provisional applications claimed as priority documents by the '810 application specifically, U.S. Provisional Application No. 60/621,148 filed Oct. 22, 2004 for Spinal Mobility Preservation Assemblies and U.S. Provisional Application No. 60/621,730 filed Oct. 25, 2004 for Multi-Part Assembly for Introducing Axial Implants into the Spine. This application incorporates by reference four co-pending and commonly assigned U.S. patent application Ser. Nos. 10/972,184, 10/972,039, 10/972,040, and 10/972,176 all filed on Oct. 22, 2004. These four applications claim priority to another United States Provisional Application, Application No. 60/558,069 filed Mar. 31, 2004. and the provisional is incorporated by reference. U.S. patent application Ser. No. 11/199,541 filed Aug. 8, 2005 and U.S. Provisional Application No. 60/599,989 filed Aug. 9, 2004 which is claimed as a priority document for the '541 are both incorporated by reference.

While a number of applications have been incorporated by reference to provide additional detail it should be noted that these other applications (including those that have subsequently issued as patents) were written at an earlier time and had a different focus from the present application. Thus, to the extent that the teachings or use of terminology differ in any of these incorporated applications from the present application, the present application controls.

BACKGROUND OF THE INVENTION

Field of the Invention

This invention relates generally to improved cutters and methods for preparing treatment sites within the spine, such at the intervertebral space between two adjacent vertebral bodies for subsequent therapeutic procedures including therapies where fusion of the two adjacent vertebral bodies is not desired such as therapies for the implantation of motion preservation devices into the spine.

Overview

The present invention is an extension of work in a series of patent applications (some now issued patents) with a common assignee. Much of the work is described in great detail in the many applications referenced above and incorporated by reference into this application. Accordingly, the background of the invention provided here does not repeat all of the detail provided in the earlier applications, but instead highlights how the present invention adds to this body of work.

The spinal column is a complex system of bone segments (vertebral bodies and other bone segments) which are in most cases separated from one another by discs in the intervertebral spaces (sacral vertebrae are an exception). FIG. 1 shows the various segments of a human spinal column as viewed from the side. In the context of the present disclosure, a "motion segment" includes adjacent vertebrae, i.e., an inferior and a superior vertebral body, and the intervertebral disc space separating said two vertebral bodies, whether denucleated space or with intact or damaged spinal discs. Unless previously fused (or damaged), each motion segment contributes to the overall flexibility of the spine contributes to the overall ability of the spine to flex to provide support for the movement of the trunk and head.

The vertebrae of the spinal cord are conventionally subdivided into several sections. Moving from the head to the tailbone, the sections are cervical 104, thoracic 108, lumbar 112, sacral 116, and coccygeal 120. The individual vertebral bodies within the sections are identified by number starting at the vertebral body closest to the head. The trans-sacral approach is well suited for access to vertebral bodies in the lumbar section and the sacral section. As the various vertebral bodies in the sacral section are usually fused together in adults, it is sufficient and perhaps more descriptive to merely refer to the sacrum rather than the individual sacral components.

It is useful to set forth some of the standard medical vocabulary before getting into a more detailed discussion of the background of the present invention. In the context of the this discussion: anterior refers to in front of the spinal column; (ventral) and posterior refers to behind the column (dorsal); cephalad means towards the patient's head (sometimes "superior"); caudal (sometimes "inferior") refers to the direction or location that is closer to the feet. As the present application contemplates accessing the various vertebral bodies and intervertebral spaces through a preferred approach that comes in from the sacrum and moves towards the head, proximal and distal are defined in context of this channel of approach. Consequently, proximal is closer to the beginning of the channel and thus towards the feet or the surgeon, distal is further from the beginning of the channel and thus towards the head, or more distant from the surgeon. When referencing tools including cutters, distal would be the end intended for insertion into the access channel and proximal refers to the other end, generally the end closer to the handle for the tool.

The individual motion segments within the spinal columns allow movement within constrained limits and provide protection for the spinal cord. The discs are important to cushion and distribute the large forces that pass through the spinal column as a person walks, bends, lifts, or otherwise moves. Unfortunately, for a number of reasons referenced below, for some people, one or more discs in the spinal column will not operate as intended. The reasons for disc problems range from a congenital defect, disease, injury, or degeneration attributable to aging. Often when the discs are not operating properly, the gap between adjacent vertebral bodies is reduced and this causes additional problems including pain.

A range of therapies have been developed to alleviate the pain associated with disc problems. One class of solutions is to remove the failed disc and then fuse the two adjacent vertebral bodies together with a permanent but inflexible spacing, also referred to as static stabilization. One estimate is that in 2004 there were an estimated 300,000 fusion operations throughout the world. Fusing one section together ends the ability to flex in that motion segment. While the loss of the normal physiologic disc function for a motion segment through fusion of a motion segment may be better than continuing to suffer from the pain, it would be better to alleviate the pain and yet retain all or much of the normal performance of a healthy motion segment.

The Operation of the Spine

The bodies of successive lumbar, thoracic and cervical vertebrae articulate with one another and are separated by the intervertebral spinal discs. Each spinal disc includes a fibrous cartilage shell enclosing a central mass, the "nucleus pulposus" (or "nucleus" herein) that provides for cushioning and dampening of compressive forces to the spinal column. The shell enclosing the nucleus includes cartilaginous endplates adhered to the opposed cortical bone endplates of the cephalad and caudal vertebral bodies and the "annulus fibrosus" (or "annulus" herein) includes multiple layers of opposing collagen fibers running circumferentially around the nucleus pulposus and connecting the cartilaginous endplates. The natural, physiological nucleus includes hydrophilic (water attracting) mucopolysaccharides and fibrous strands (protein polymers). The nucleus is relatively inelastic, but the annulus can bulge outward slightly to accommodate loads axially applied to the spinal motion segment.

The intervertebral discs are anterior to the spinal canal and located between the opposed end faces or endplates of a cephalad and a caudal vertebral bodies. The inferior articular processes articulate with the superior articular processes of the next succeeding vertebra in the caudal (i.e., toward the feet or inferior) direction. Several ligaments (supraspinous, interspinous, anterior and posterior longitudinal, and the ligamenta flava) hold the vertebrae in position yet permit a limited degree of movement. The assembly of two vertebral bodies, the interposed, intervertebral, spinal disc and the attached ligaments, muscles and facet joints is referred to as a "spinal motion segment"

The relatively large vertebral bodies located in the anterior portion of the spine and the intervertebral discs provide the majority of the weight bearing support of the vertebral column. Each vertebral body has relatively strong, cortical bone layer forming the exposed outside surface of the body, including the endplates, and weaker, cancellous bone in the center of the vertebral body.

The nucleus pulposus that forms the center portion of the intervertebral disc consists of 80% water that is absorbed by the proteoglycans in a healthy adult spine. With aging, the nucleus becomes less fluid and more viscous and sometimes even dehydrates and contracts (sometimes referred to as "isolated disc resorption") causing severe pain in many instances. The spinal discs serve as "dampeners" between each vertebral body that minimize the impact of movement on the spinal column, and disc degeneration, marked by a decrease in water content within the nucleus, renders discs ineffective in transferring loads to the annulus layers. In addition, the annulus tends to thicken, desiccate, and become more rigid, lessening its ability to elastically deform under load and making it susceptible to fracturing or fissuring, and one form of degeneration of the disc thus occurs when the annulus fissures or is torn. The fissure may or may not be accompanied by extrusion of nucleus material into and beyond the annulus. The fissure itself may be the sole morphological change, above and beyond generalized degenerative changes in the connective tissue of the disc, and disc fissures can nevertheless be painful and debilitating. Biochemicals contained within the nucleus are enabled to escape through the fissure and irritate nearby structures.

Various other surgical treatments that attempt to preserve the intervertebral spinal disc and to simply relieve pain include a "discectomy" or "disc decompression" to remove some or most of the interior nucleus thereby decompressing and decreasing outward pressure on the annulus. In less invasive microsurgical procedures known as "microlumbar discectomy" and "automated percutaneous lumbar discectomy", the nucleus is removed by suction through a needle laterally extended through the annulus. Although these procedures are less invasive than open surgery, they nevertheless suffer the possibility of injury to the nerve root and dural sac, perineural scar formation, re-herniation of the site of the surgery, and instability due to excess bone removal. In addition, they generally involve the perforation of the annulus.

Although damaged discs and vertebral bodies can be identified with sophisticated diagnostic imaging, existing surgical interventions and clinical outcomes are not consistently satisfactory. Furthermore, patients undergoing such fusion surgery experience significant complications and uncomfortable, prolonged convalescence. Surgical complications include disc space infection; nerve root injury; hematoma formation; instability of adjacent vertebrae, and disruption of muscle, tendons, and ligaments, for example.

As noted previously, the normal nucleus is contained within the space bounded by the bony vertebrae above and below it and the annulus fibrosus, which circumferentially surrounds it. In this way the nucleus is completely encapsulated and sealed with the only communication to the body being a fluid exchange that takes place through the bone interface with the vertebrae, known as the endplates.

The hydroscopic material found in the physiological nucleus has an affinity for water (and swells in volume) which is sufficiently powerful to distract (i.e., elevate or "inflate") the intervertebral disc space, despite the significant physiological loads that are carried across the disc in normal activities. These forces, which range from about 0.4× to about 1.8× body weight, generate local pressure well above normal blood pressure, and the nucleus and inner annulus tissue are, in fact, effectively avascular.

Details of specific advantages and specific motion preservation devices including methods for implanting motion preservation devices are described in various pending applications including Ser. Nos. 11/586,338 and 11/586,486 referenced above. The reader may select to read these details but there is not a need to repeat that material in its entirety here.

While the cutters described below may be used in other surgical procedures including spinal surgery that does not approach an intervertebral space via an axial approach but comes to the space through an anterior or a posterior approach. The cutters may be used in surgical procedures with the motion preservation devices inserted axially within the spine, following either partial or complete nucleectomy and possibly through a cannula that is docked against the sacrum, into a surgically de-nucleated disc space, from said access point across a treatment zone. In such a procedure, the introduction of the spinal motion preservation assembly of the present disclosure is accomplished without the need to surgically create or deleteriously enlarge an existing hole in the annulus fibrosus of the disc.

Design of cutter blades includes considerations in many cases of the efficiency with which the cutter blade prepares the contents of the nucleus for removal by cutting (slicing, tearing, or some combination of the two). It is generally desirable to allow a surgeon to work quickly and efficiently to reduce the time of surgery which has benefits in reducing the use of expensive resources such as the surgical team and the surgical suite and also reduces the length of time that a patient is kept under anesthesia.

A cutter blade that must be replaced frequently may be less desirable than a cutter blade with similar characteristics that is more durable and thus may be used longer without needing to be replaced.

A cutter blade that fails in a mode where all the pieces of the failed cutter blade may be easily removed from the intervertebral disc space and the patient body may be preferred over a similar cutter blade that does not have this characteristic.

SUMMARY OF THE DISCLOSURE

Disclosed herein are cutter assemblies for use with cutter blades made of shape memory materials. The cutter blades may be deployed in the interior of an intervertebral disc space and rotated relative to a central axis of the cutter assembly which is substantially aligned with a centerline of an axis channel. Rotation of a cutter blade as part of a cutter assembly within an intervertebral disc space cuts the material present there for removal from the intervertebral disc space. Cutter blades with different attributes (such as throw length, cutter blade angle, type and location of blade edges) are adapted to achieve different objectives within the intervertebral disc space. Some cutter blades are adapted to promote bleeding of cartilage and vertebral body endplates and some cutter blades are adapted to avoid causing such bleeding as different therapeutic procedures seek or seek to avoid such bleeding.

The use of a hollow ground to enhance the cutting action of a blade edge is described in connection with the creation of cutter blades.

A variety of thin cutter blades are described which may be used in the interior of a thin intervertebral disc (having a reduced distance between the endplates of the adjacent vertebral bodies).

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The invention can be better understood with reference to the following figures. The components in the figures are not necessarily to scale, emphasis instead being placed upon illustrating the principles of the invention. Moreover, in the figures, like reference numerals designate corresponding parts throughout the different views.

FIGS. 4A-4B are views of a cutter assembly.

FIG. 6A-6D provides additional views of a cutter assembly including stops that limit the range of travel of the cutter sheath.

FIG. 15 shows a thin cutter blade with the cutting edges recessed from the exterior surfaces of the thin cutter blade by having adjacent blade edges from the distal arm and the proximal arm.

FIG. 16 shows a "L" cutter blade which used a single arm rather than a pair of arms.

FIG. 17 shows a number of views of an "L" cutter blade that is much like "L" cutter blade except that the cutting edges are on the proximal side of the "L" cutter blade.

FIG. 20 is the distal end of a cutter shaft.

FIG. 21 is an enlarged detail of FIG. 20.

FIG. 22 is a cross section of the distal end of the cutter shaft of FIG. 20.

FIG. 23 is the distal end of a cutter shaft.

FIG. 24 is an enlarged detail of FIG. 23.

FIG. 25 is a cross section of the distal end of the cutter shaft of FIG. 23.

DETAILED DESCRIPTION

While the inventive cutters described below may be used in other surgical procedures, it is useful in context to describe how these cutters could be adopted for use in a trans-sacral approach. As noted above there are many advantages associated with a minimally invasive, low trauma trans-sacral axial approach. The trans-sacral axial approach (described and disclosed in commonly assigned U.S. Pat. Nos. 6,558,386; 6,558,390; 6,575,979; 6,921,403; 7,014,633, and 7,087,058) has a number of advantages over other routes for delivery of therapeutic devices to motion segments but there are logistical challenges to the preparation of an intervertebral disc space via an axial access channel. The process of addressing these challenges impacts certain aspects of the cutters intended for use in this manner.

Trans-Sacral Axial Access

The trans-sacral axial access method illustrated in FIG. 2, eliminates the need for muscular dissection and other invasive steps associated with traditional spinal surgery while allowing for the design and deployment of new and improved instruments and therapeutic interventions, including stabilization, motion preservation, and fixation devices/fusion systems across a progression-of-treatment in intervention.

Figure 1:
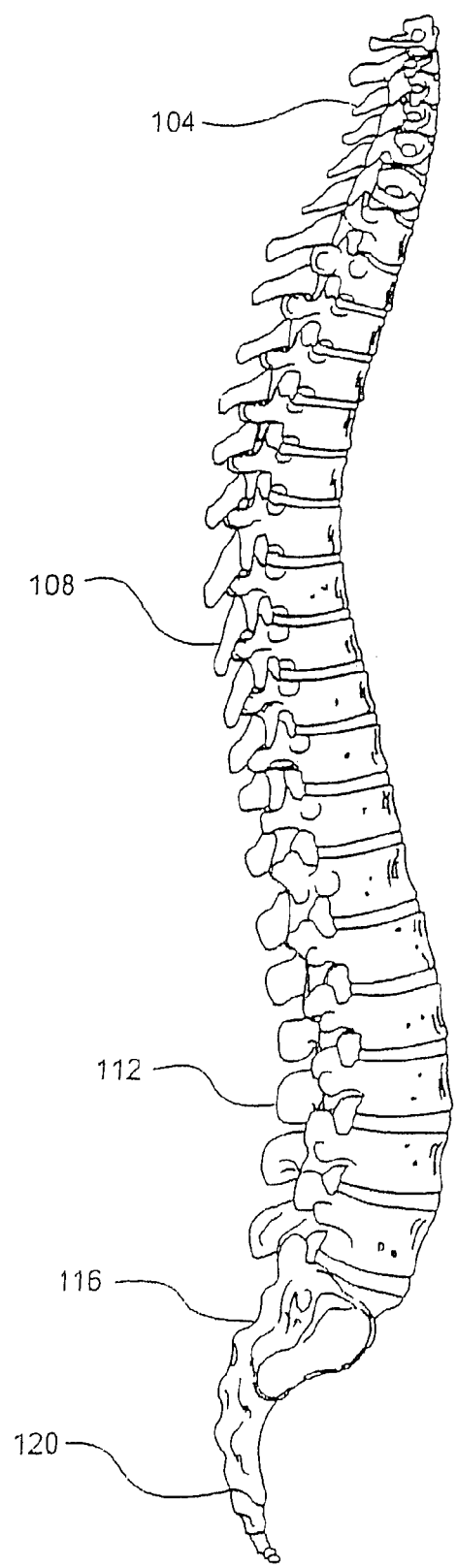
FIG. 1 identifies the sections of a human spine.
Figure 2A:
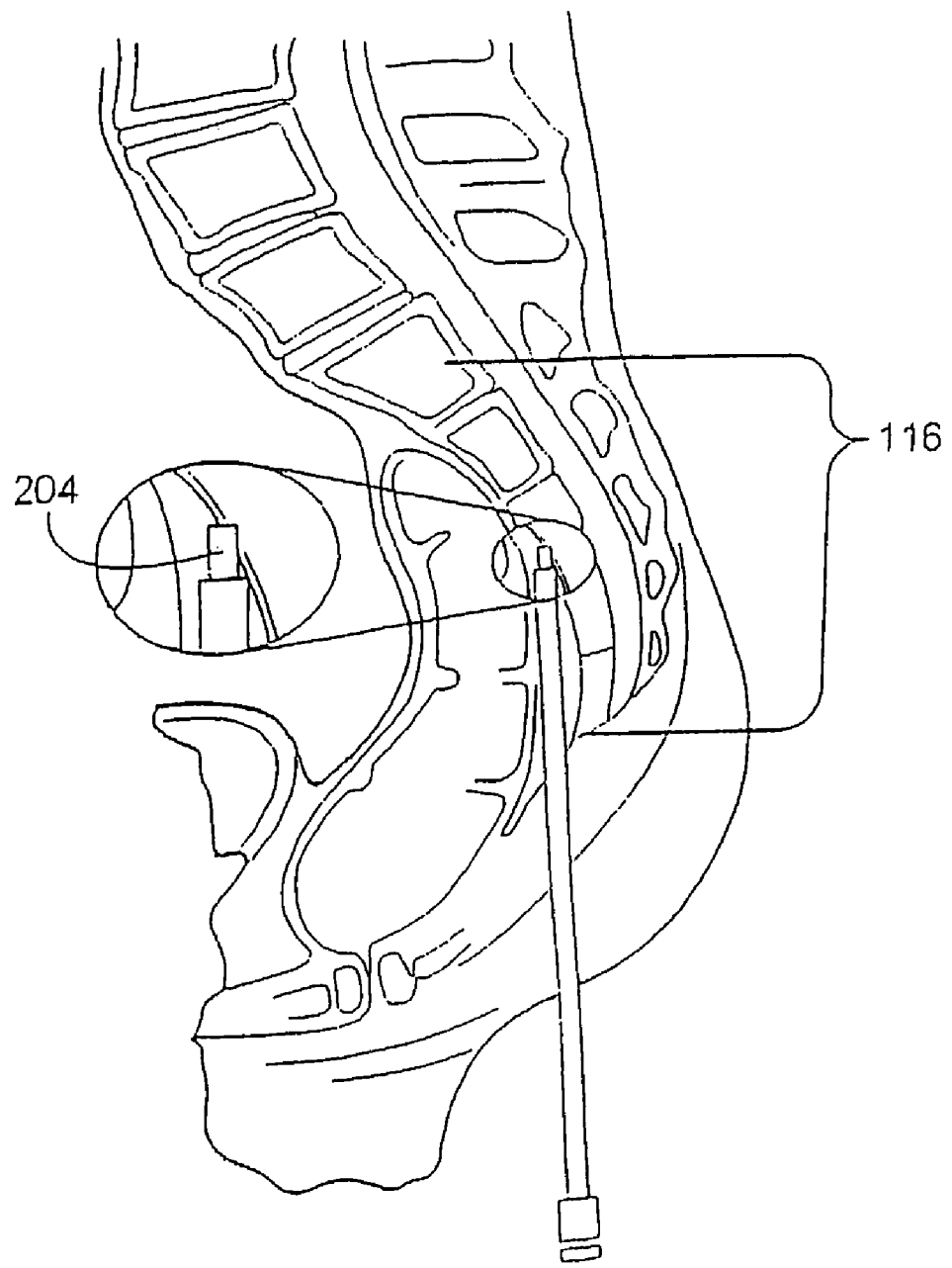
FIGS. 2(A)-(C) illustrates an anterior trans-sacral axial access method of creating an axial channel in the spine which can be used to prepare an axial channel in the spine for use with the present disclosure.
Figure 2B:
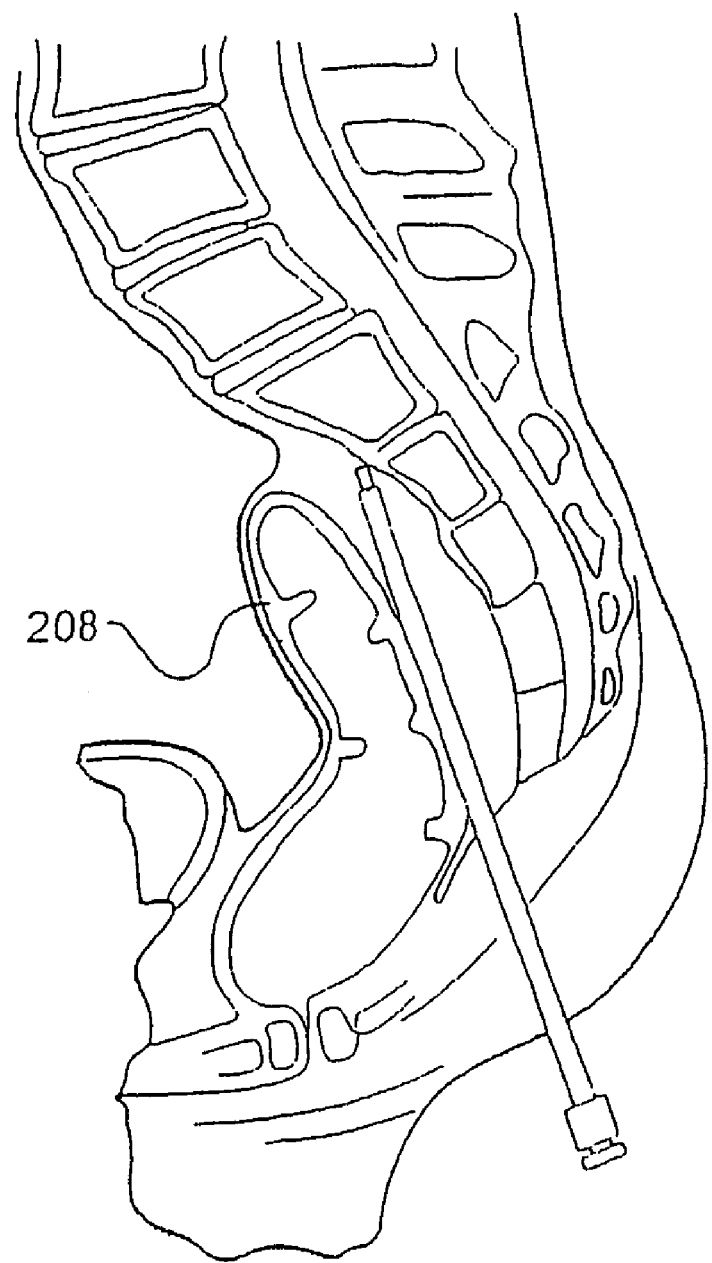
Figure 2C:
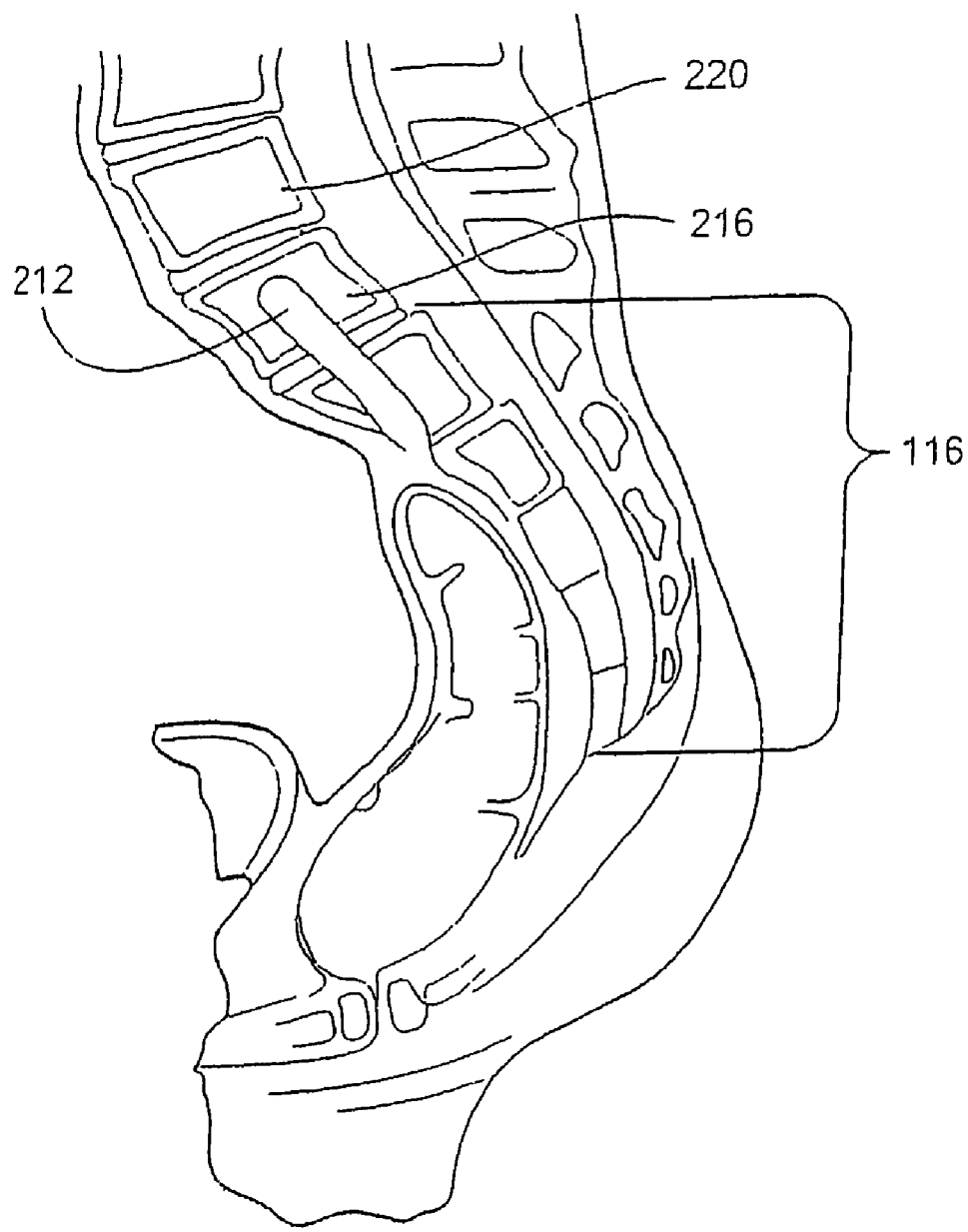

FIG. 2 provides an introductory overview of the process with FIGS. 2(a) and 2(b) showing the process of "walking" a blunt tip stylet 204 up the anterior face of the sacrum 116 to the desired position on the sacrum 116 while monitored one or more fluoroscopes (not shown). This process moves the rectum 208 out of the way so that a straight path is established for the subsequent steps. FIG. 2(c) illustrates a representative trans-sacral axial channel 212 established through the sacrum 116, the L5/sacrum intervertebral space, and into the L5 vertebra 216. If therapy is being provided to the L4/L5 motion segment then the channel would continue through the L5 vertebra 216 through the L4/L5 intervertebral space, and into the L4 vertebra 220.

The discussion of FIG. 2 is provided to provide context for the present disclosure. Previous applications (some now issued as United States patents) with common assignee have included a description of an alternative access method that is a posterior trans-sacral axial spinal approach rather than an anterior trans-sacral axial spinal approach. (See e.g. U.S. Pat. No. 6,558,386 for Axial Spinal Implant and Method and Apparatus for Implanting an Axial Spinal Implant Within the Vertebrae of the Spine as this patent describes the anterior trans-sacral axial approach illustrated in FIG. 2 and is incorporated by reference in its entirety.)

Figure 3:
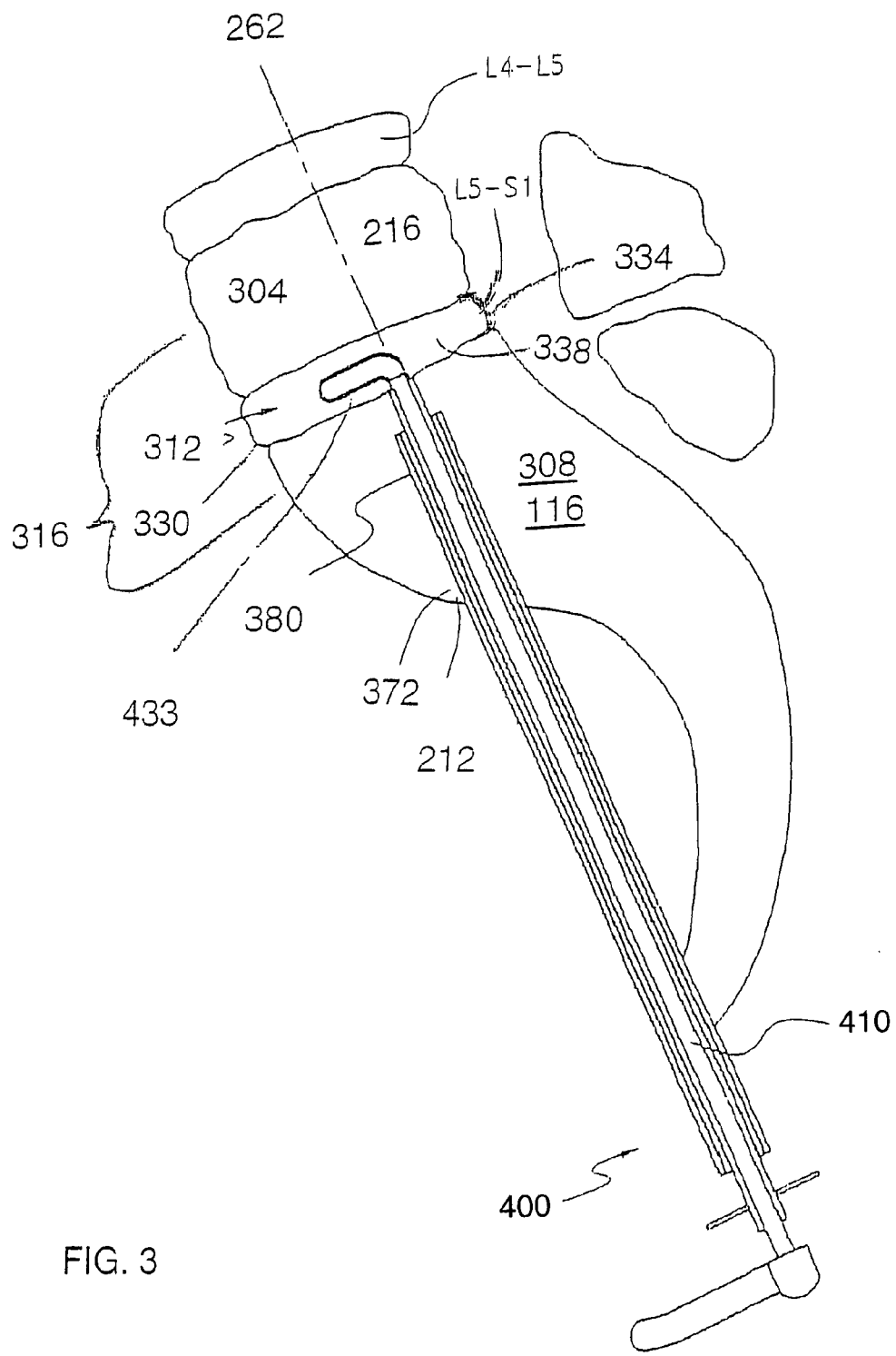
FIG. 3 shows a cutter assembly inserted into an axial channel with the cutter blade in an extended position.

Referring to FIG. 3, a cutter 400 is inserted through the axially aligned anterior tract 372 defined by the lumen of the dilator sheath 380 and the axial channel 212 which is difficult to see as the dilator sheath 380 substantially fills the axial channel 212 as it passes through the sacrum 116. (One of skill in the art will appreciate that the axial channel 212 may be extended axially by a sequence of steps so that the length of an axial channel in one Figure may be different from another Figure such that the axial tract may include additional vertebral bodies or intervertebral disc spaces). One of skill in the art will appreciate that due to anatomical differences the axial channel for some therapies may miss the sacrum and may enter through another portion of the spine.

As shown in FIG. 3, motion segment 316 that includes the proximal vertebra 308 (the sacrum 116), the intervertebral space 312 (in this case the L5-S1 space with disc 330, annulus fibrosus 334 and nucleus 338), the distal vertebra 304 (in this case L5 216). The cutter 400 comprises a cutting blade (e.g., cutter blade 453 which refers collectively to any blade configuration) which is remotely manipulable. The manipulations of the cutter blade 453 may include retracting the cutter blade 453 into the cutter assembly 400 so that the maximum radius of the cutter assembly 400 is reduced and the cutter assembly with the retracted blade 453 may be advanced through the axial channel 212. After reaching the location where the cutter blade 453 is to be operated, the cutter blade 453 may be extended.

As shown in FIG. 3, the centerline 262 of the cutter 400 is very close to the centerline of the axial channel 212 due to the fit of the dilator sheath 380 in the axial channel 212 and the fit of the cutter 400 within the dilator sheath 380. When the cutter blade 453 is extended as shown in FIG. 3 the cutter blade is substantially transverse to the centerline 262 of the cutter 400. The extended cutter blade 453 is extended laterally into the nucleus 338 of the spinal disc 330.

The cutter shaft 410, cutter sheath 430 (shown in FIG. 4) and the handle components are preferably co-configured to enable the cutter blade 453 and the cutter shaft 410 to which it is attached be able to be "pushed-pulled" so as to retract the cutter blade 453 into the cutter sheath and then extend the cutter blade 453 from the distal end of the cutter sheath as needed. More specifically, the cutter blade edges(s) of the cutter blade 453 are retracted into the cutter sheath 430 (FIG. 4) for delivery into the intervertebral disc space 312. Once the cutter 400 is in position, the cutter blade 453 is extended distally and rotated using the handle to cut tissue within the intervertebral disc space 312. After completing the cutting task or until the cutter blade needs replacement, the cutter blade 453 is again retracted into the cutter sheath 430 (FIG. 4) for removal of the cutter assembly unit 400 from the axial channel 212.

The cutter assembly 400, cutter blade 453 and cutter assembly shaft 410 are shown schematically in FIGS. 4A-4B and not necessarily to scale to one another or to the axial channel 212.

Cutters can be used to perform nucleectomies via insertion into a disc space to excise, fragment and otherwise loosen nucleus pulposus and cartilage from endplates from within the disc cavity and from inferior and superior bone endplate surfaces. As noted within this disclosure, damage to or removal of cartilage tends to cause bleeding within the intervertebral disc space 312. Bleeding tends to promote bone growth, which may be desired in a fusion type therapy but may be undesirable in other therapies, including therapies that call for the implantation of a motion preservation device into the motion segment 316.

With reference to the exemplary embodiments of FIGS. 4A-B, the cutter assembly 400 (also referred to as simply a cutter) includes: a cutter shaft 410 with a distal end 412 and a proximal end 414; a cutter blade 453 connected to the distal end 412 of the cutter shaft 410; a handle 416 connected to the proximal end 414 of the cutter shaft by an attachment process such as a set screw or pin; a cutter sheath 430 placed concentrically over the shaft 410; and a shaft sleeve 418 (shown in subsequent drawings).

Figure 5A:
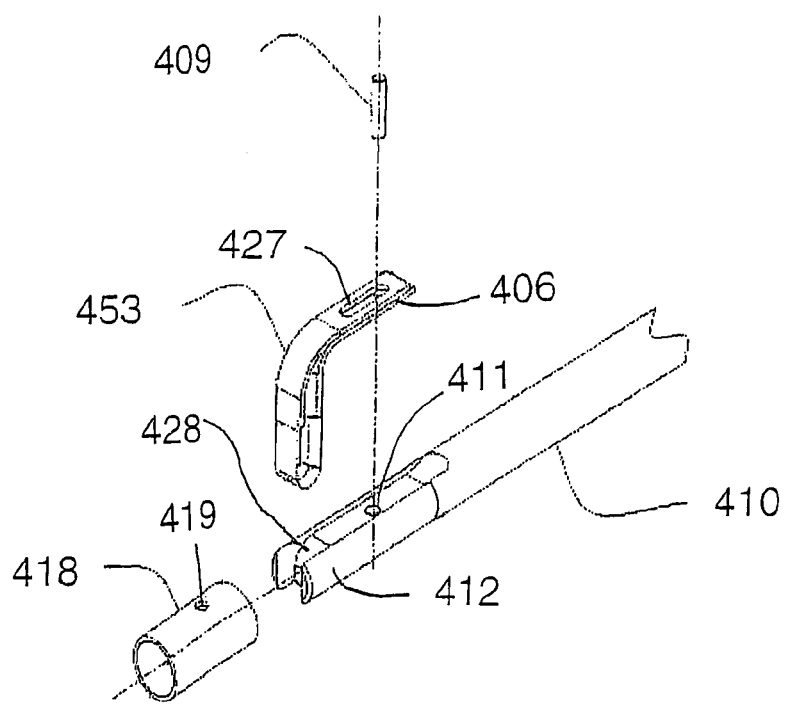
FIG. 5A-5B shows one method for connecting a cutter blade to a cutter shaft.
Figure 5B:
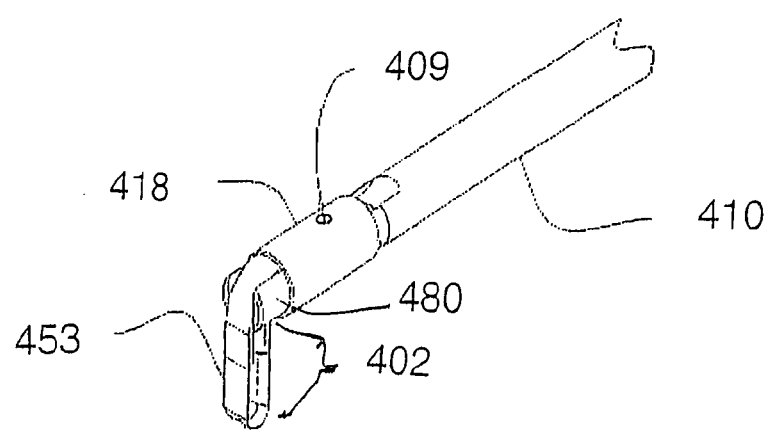

FIGS. 5A-5B illustrate one method of connecting a cutter blade 453 to a cutter shaft 410. Before the pin 409 is inserted, the longitudinal portion 406 of the cutter blade 453 is placed into a slot 413 near the distal end 412 of the cutter shaft 410. The cutter blade slot 427 may be aligned with the cutter shaft hole 411 within the shaft slot 413. A pin 409 may be placed through a shaft sleeve hole 419 in a shaft sleeve 418 and through a cutter blade slot 427 (visible in FIG. 5A), a cutter blade hole 407 on the opposite side of the longitudinal portion 406 of the cutter blade 453 (best seen in FIG. 10A). The pin passes through cutter blade hole 407 and into a cutter shaft hole 411 in a cutter shaft slot 413.

The shaft slot 413 is dimensioned to accommodate a cutter blade 453. The width of the slot 413 is approximately the same as the width of the longitudinal portion 406 of the cutter blade 453. The curvature 428 at the distal end of the slot 413 accommodates the curvature of the cutter blade 453 between the longitudinal portion 406 and the portion of the cutter blade that may be extended 402 (also known as the cutter blade arm 402) (which defines the reach or throw of the cutter blade 453). The slot 413 provides torsional support to the cutter blade arm 402 while the curvature 428 at the distal end of the slot 413 provides axial support to the cutter blade arm 402 to work in conjunction with cutter blade edge geometries to reinforce the cutter blade 453. The cutter shaft extension 480 discussed in more detail below provides additional support to the cutter blade 453 to reduce the tendency of the cutter blade to flex when rotated into tissue.

The shaft sleeve 418 when pinned, effectively serves to align and fix the shaft 410 and the longitudinal portion 406 of the cutter blade 453. For purposes of illustration, the pin 409 that fixes the cutter blade 453 to the shaft 410 may be approximately 0.06 inches (1.5 mm) in diameter.

As cutter blade hole 407 is pinned to the cutter blade shaft 410, the cutter blade 453 is affixed to the cutter blade shaft 410. The cutter blade slot 427 allows some relative motion of the slotted portion of the longitudinal portion 406 relative to the pinned portion of the longitudinal portion 406 to accommodate the change of shape of the cutter blade 453 as it goes from sheathed to extended and back to sheathed.

The rest of the cutter 400 components can be fixedly secured to each other using any known suitable fixation mechanisms.

FIGS. 6A-6D provides a series of views of a cutter assembly 400. FIG. 6A is a top view of the cutter assembly 400. FIG. 6B is a rear view of the cutter assembly 400. FIG. 6C is a cross section of FIG. 6B. FIG. 6D is a enlarged portion of FIG. 6C.

As shown an FIGS. 6A and 6D, the slot in the cutter shaft 410 may be oriented so that the handle 416 is aligned with the blade arm 402 (when extended). While not required, this relationship between the handle and blade is a useful way to allow the surgeon to keep track of the position of the extended blade arm 402 by knowing rotational position of the handle 416.

As best seen in FIG. 6D, the travel range 440 of the cutter sheath 430 is limited at the proximal end by a proximal end stop 444 attached to the cutter shaft 410. The travel range 440 of the cutter sheath 430 is limited at the distal end by a shoulder 448 on the cutter shaft 410.

One of skill in the art will appreciate that while the cutter blades 453 are to be used with a single patient and then disposed, that, certain components such as the handle 416, cutter shaft 410, and cutter sheath 430 may be reusable. The handle and cutter shaft could be made as one integral component.

A sleeve or internal sheath liner (not shown) may be inserted inside the cutter sheath to reduce friction. The cutter blade 453 may be formed from a shape memory alloy including a nickel-titanium shape memory alloy such as Nitinol™.

The cutter sheath 430 may be made from an appropriate grade of stainless steel. To reduce the friction between the cutter blade 453 and the inner surface of the cutter sheath 430, a dry lubrication such as poly-tetrafluoroethylene (PTFE) may be used. Alternatively, the sleeve or internal sheath liner may be made of a material with a coefficient of friction that is lower than the cutter blade. If this component is to be reused, it may be chosen for its ability to withstand multiple sterilization cycles. Ultra-high molecular weight polyethylene (UHMWPE) is one such material.

Figure 7:
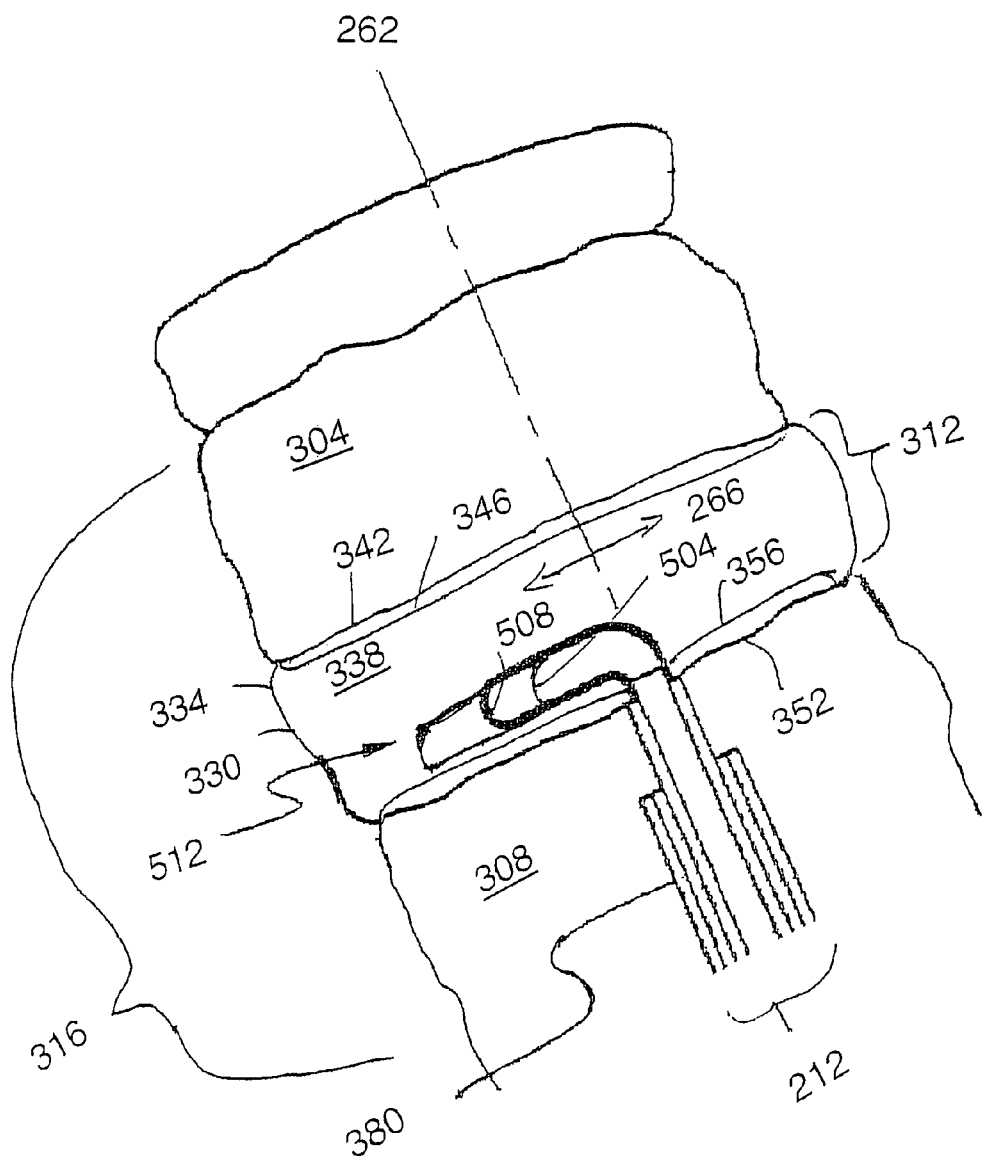
FIG. 7 addresses the concept of a series of cutter blades of different throw lengths within an intervertebral disc space

After this introduction to cutters and cutter components, it is useful to discuss why a sequence of cutters may be used while preparing the interior of an intervertebral disc space 312. FIG. 7 shows a first example. In FIG. 7 a motion segment 316 including a distal vertebral body 304, an intervertebral disc space 312 (with a intervertebral disc 330 including an annulus fibrosus 334, and nucleus pulposus 338 and bounded by the endplates), and a proximal vertebral body 308 are shown. For purposes of this example, it is not important which vertebral bodies are involved beyond the need for them to be adjacent vertebral bodies.

FIG. 7 includes the endplate 342 of the distal vertebral body 304 and a representation of the layer of cartilage 346 located on the endplate 342 which defines one portion of the intervertebral disc space 312. Assuming the route of access is a trans-sacral axial access, from the point of reference of the intervertebral disc space 312, endplate 342 would be the superior endplate. Likewise FIG. 7 includes the endplate 352 of the proximal vertebral body 308 and a representation of the layer of cartilage 356 located on the endplate 352 which defines one portion of the intervertebral disc space 312. Assuming the route of access is a trans-sacral axial access, from the point of reference of the intervertebral disc space 312, endplate 352 would be the inferior endplate.

One of skill in the art will recognize that the inclusion of the cartilage layers 346 and 356 is for purposes of discussing the use of cutters and is not intended to be an anatomically correct and appropriately dimensioned representation of cartilage.

The position of the cutter within the intervertebral disc space may be visible to the surgeon under real-time fluoroscopic imaging (possibly both anterior/posterior and lateral imaging).

In order to illustrate a point, FIG. 7 includes representations of three different cutter blades 504, 508, and 512 of differing throw lengths. One of ordinary skill in the art will appreciate that one method for cutting the nucleus 338 would use a series of cutter blades (504, 508, 512, and possibly another longer blade) to gradually cut the nucleus 338. One of ordinary skill in the art will understand that these three blades of different throw lengths (sometime called reaches) would be used sequentially from shorter to longer and it is only for the point of illustration that three different blade lengths are shown simultaneously in FIG. 7. To provide context, the reach of a series of cutter blades used in a particular procedure may range from 0.40 inches for a small cutter blade to 0.70 inches for a large cutter blade. One of skill in the art will recognize that these ranges are illustrative and could be different. It will be understood that the optimum throw for cutter blades depends on several factors, including patient anatomy and (axial) entrance point into the disc space, as well as issues related to sagittal symmetry of the spinal disc. Moreover, for safety reasons, it may be desirable to limit the length of the cutter blade to preclude a throw that is too close to the disc edge, in other words to avoid making contact between the cutter blade and the annulus fibrosus to preclude compromising the annulus fibrosus.

Note that the cutter blades 504, 508, and 512 when extended are transverse to the centerline of the cutter 262 and parallel to the axis 266 that is perpendicular to cutter blade centerline 262. The cutter blades are also close to parallel to the endplates 342 and 352 and the layers of cartilage 346 and 356.

In this example, the successively longer cutter blades 504 508, and 512, could be rotated 360 degrees or more around the centerline 262. Some surgeons may prefer to work on one segment at a time by rotating the cutter handle a fraction of 360 degrees (perhaps approximately 90 degrees) then rotating the cutter handle in the opposite direction to return to the position occupied by the cutter. Thus, the process tends to proceed while working on radial quadrants. Sometimes this short movement is compared to the movement of windshield wipers on an automobile.

In addition to using a series of cutter blades with sequentially increasing throws, the surgeon will need to adjust the axial position of the cutter blade by sliding the cutter forward (in the direction towards distal) relative to the motion segment so that the cutter blade move sequentially closer to the cartilage 346 on the endplate 342 on the distal vertebral body 304. The surgeon may opt to create a first space relatively close to the proximal vertebral body by using a sequence of cutters of increasing throws then repeating the process with the cutter extended further into the nucleus (and repeating the sequence of blades of increasing throws).

Alternatively, the surgeon may choose to use one or more cutters with a first throw to create a space approximating a cylinder that is substantially the height of the space between the two layers of cartilage and a radius approximately equal to a first blade throw. This process may involve the use of a radial cutter blade with a given throw length followed by one or more cutter blades at a different blade angle(s) (for example 45 degrees) but the same throw length. Once the cutting is complete for a given throw length, the surgeon moves to cutter blades of a longer throw length starting again with a radial cutter blade. This process may be repeated with cutter blades of increasing blade throws until the desired amount of space is created.

The nature of the therapeutic procedure and the patient anatomy will determine the maximum cutter blade throw length required. Certain procedures may tend to use a greater number of cutter blade throw lengths to make smaller incremental increases in throw length. Other procedures may simply use a small throw length then move to the maximum throw length needed to prepare the intervertebral disc space.

As the nucleus material is cut, the surgeon may periodically remove the cutter from the axial channel and use any appropriate tissue extractor tool. U.S. patent application Ser. No. 10/972,077 (referenced above) describes several retractable tissue extractors that may be used for this purpose.

U.S. patent application Ser. No. 10/972,077 (referenced above) noted that when preparing a intervertebral disc space for a fusion procedure, it can be advantageous to use cutters to scrape away the cartilaginous endplate and roughen the vascularized vertebral body so as to cause bleeding, which is desirable in order to facilitate bone growth and to promote fusion of the vertebral bodies of the relevant motion segment.

However, not all therapeutic procedures seek to obtain such bleeding to promote fusion. It is unavoidable to disturb the a portion of endplate 352 of the proximal vertebral body as the axial channel is created through the endplate 352 and it is likewise unavoidable to disturb a portion of the cartilage 356 in the immediate vicinity of the axial channel (likewise the endplate 342 and cartilage 346 of the distal vertebral body 304 if the axial channel 212 (FIG. 2C) is extended into the distal vertebral body 304. However, the unavoidable disturbance of a small portion of an endplate and cartilage does not remove the advantage within certain procedures of avoiding damage to other portions of the cartilage and endplate.

Figure 8:
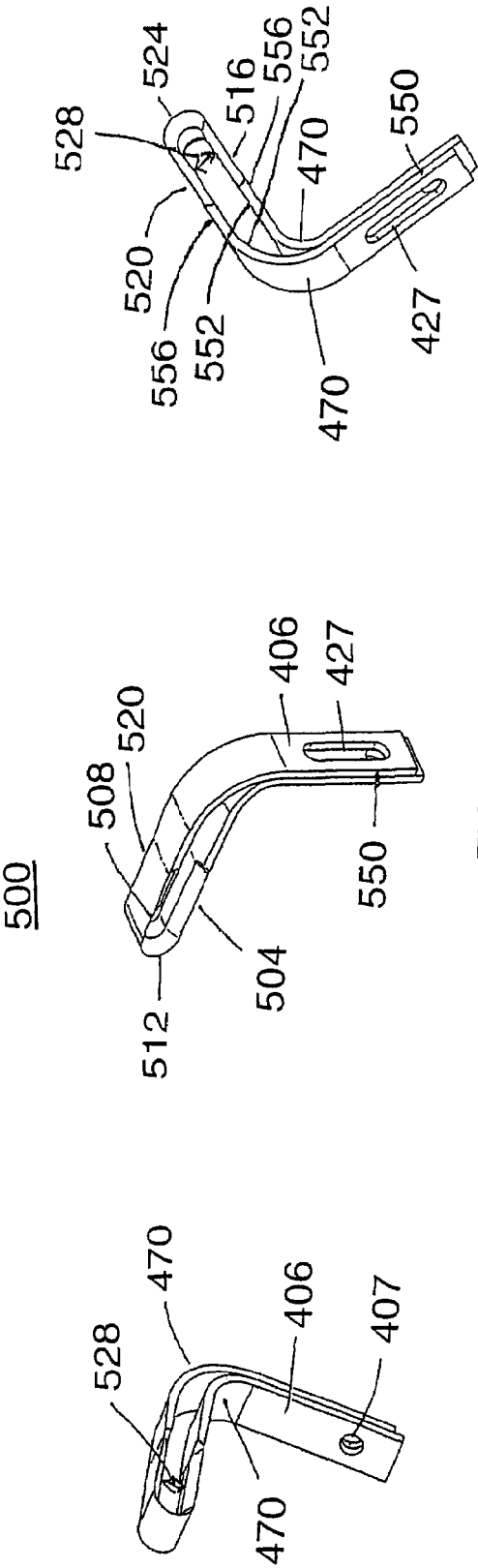
FIGS. 8A-8D shows a series views of a closed loop cutter blade that is adapted to scrape away the cartilaginous endplate and roughen the vascularized vertebral body so as to cause bleeding.

FIG. 8 shows a series views of a closed loop cutter blade 500 that is adapted to scrape away the cartilaginous endplate and roughen the vascularized vertebral body so as to cause bleeding. Visible are the cutter blade hole 407 and the cutter blade slot 427. The cutter blade arm 402 is joined to the longitudinal portions 406 by a pair of transitional sections 470. While the precise position is not particularly relevant, in the area where the two transitional sections 470 meet the two longitudinal sections 406, the two ends of the cutter blade meet. This point of contact could be deemed the place where the loop is closed. However, it may be simpler to call the loop closed at 550 which is placed at cutter blade hole 407 and the currently adjacent portion of cutter blade slot 427 as those two are joined when the cutter blade is attached to the cutter assembly at the blade shaft (See FIG. 5) The closed loop adds a safety feature in that in the event of a break in cutter blade 500 while inserted into an intervertebral disc space, the cutter blade 500 will remain connected to the cutter shaft through either the portion of the cutter blade with the slot 427 (in this case the distal arm 560 of the cutter blade 500) or the portion of the cutter blade with a hole 407 (in this case the proximal arm 564 of the cutter blade 500). (One of skill in the art will recognize that the distal arm 560 meets the proximal arm 564 at the blade tip 548). As all parts of the cutter blade 500 are connected to the cutter shaft such that in the event of a break in the cutter blade, the parts can be removed from the intervertebral disc space by prompt removal of the cutter assembly.

Surgeons may note a break in the cutter blade either by a change in feel in the operation of the cutter or by a visible change in the cutter blade as indicated in the real-time fluoroscopic imaging. While cutter blades and the process for using cutter blades are designed with the intent to avoid breaking cutter blades within the patient's body, it is useful to provide this safety feature given the nature of the use of the cutter blades which come in contact with vertebral bodies.

Cutter blade 500 can be said to have six different cutting edges 504, 508, 512, 516, 520, 524. Three cutting edges 504, 508, 512 on one side and three cutting edges 516, 520, 524 on the other side. Edges 504 and 516 are on the proximal portion 536 of the blade arm 402 of the cutter blade 500, that is the portion of the blade arm that is closer to the handle 416 (FIG. 4A) than the other portion of the closed loop that is the distal portion 542 of the blade arm 402.

When inserted into the intervertebral disc space, the exterior of the proximal portion 536 will generally face the endplate on the proximal vertebral body (whether or not the proximal portion is parallel to the endplate). Edges 508 and 520 are on the distal portion 542 of the blade arm 402. When inserted into the intervertebral disc space, the exterior of the distal portion 542 will generally face the endplate on the distal vertebral body (whether or not the distal portion 542 is parallel to the endplate). Edges 512 and 524 are on the tip 548 of the cutter blade 500 between the distal portion 542 and the proximal portion 536 of the blade arm 402 and connecting the distal arm 560 and the proximal arm 564.

The cutting edges along the proximal portion 536 and the distal portion 542 of the blade arm 402 do not extend over the entire blade arm 402. As indicated in FIG. 7 it is contemplated that a series of cutter blades of increasing length will be used so that the cutter blade edges do not need to extend over the entire range that was previously cut by a previous cutter blade.

Note that the sides of a cutter blade are not necessarily flat. The sides (sometimes called faces) have features that are visible when looking at that side or face of the object (just as the indentations on one of the six faces of a single die from a pair of dice are visible when looking at that face or side of the die).

In each case, the six cutting edges are on the outer perimeter 556 of the closed loop rather than on the inside perimeter 552 as the outer perimeter 556 is the better choice for edge placement in order to contact the cartilage on an endplate. By placing the cutting edges on the outer perimeter 556 of the closed loop, the cutter blade 500 is adapted to maximize the effectiveness of the cutter blade in cutting either the cartilage 356 (FIG. 7) on the proximal endplate 352 (likely to be the inferior endplate when viewed in context of the intervertebral disc space 312) or the cartilage 346 (FIG. 7) on the distal endplate 342 (likely to be the superior endplate when viewed in the context of the intervertebral disc space 312).

By having cutting edges on both sides of cutter blade 500, the surgeon may cut nucleus material while rotating the cutter blade in the clockwise direction and also while rotating the cutter blade in the counter-clockwise direction. (Clockwise and counterclockwise are dependent on orientation. One way of defining clockwise would be as viewed from the cutter while looking from proximal towards distal end of the cutter assembly. This would match the way the surgeon would view rotation of the cutter handle.)

While being bidirectional is a useful feature, not all cutter blades must have cutting edges on both sides. Some cutter blades may have one type of cutting edge on one side and a second type of cutter blade on the second side. While it may be advantageous for some cutter blades to have blade edges on the tips of the cutter blade, some cutter blades may not have a blade edge in the tip or may have a different blade edge type in the tip 548 than in the distal portion 542 and proximal portion 536.

The cutting blade 500 has a gap 528 within the closed loop that may allow material to pass through the gap while the cutter blade 500 is being rotated within the intervertebral disc space 312. This may add another aspect to the cutting action while reducing the resistance to the cutter blade 500 moving through the intervertebral disc space 312. Other cutter blades may have less of a gap between the distal and proximal portions or no gap at all.

A cutter blade without a gap large enough to allow material to pass through the gap in the inside perimeter of the close loop receives benefit from the closed loop as noted above in that having the closed loop connected to the cutter shaft provides two points of connection for the cutter blade and provides at least one point of connection from each part of the cutter blade to the cutter shaft 410 in the event of a break in the cutter blade.

Hollow Ground Cutter Blades

FIGS. 9A-9D show four views of a cutter blade 560 that is similar to cutter blade 500 discussed above. These drawings do not show cutter blade holes or cutter blade slots as that is not the focus of these drawings and some cutter blades may be connected to a cutter shaft with other conventional methods that do not involve a pin or rivet through a cutter blade hole or holes or a combination of a cutter blade hole and a cutter blade slot.

What is new in cutter blade 560 over cutter blade 500 is a hollow ground visible on the top of the cutter blade 560 as element 564 between blade edges 508 and 520 and as element 568 between blade edges 524 and 512. While not visible in this set of figures, the hollow ground may be added between edge 504 (not visible here) and edge 516 on the proximal portion 536 of the blade arm 402.

Figure 9:
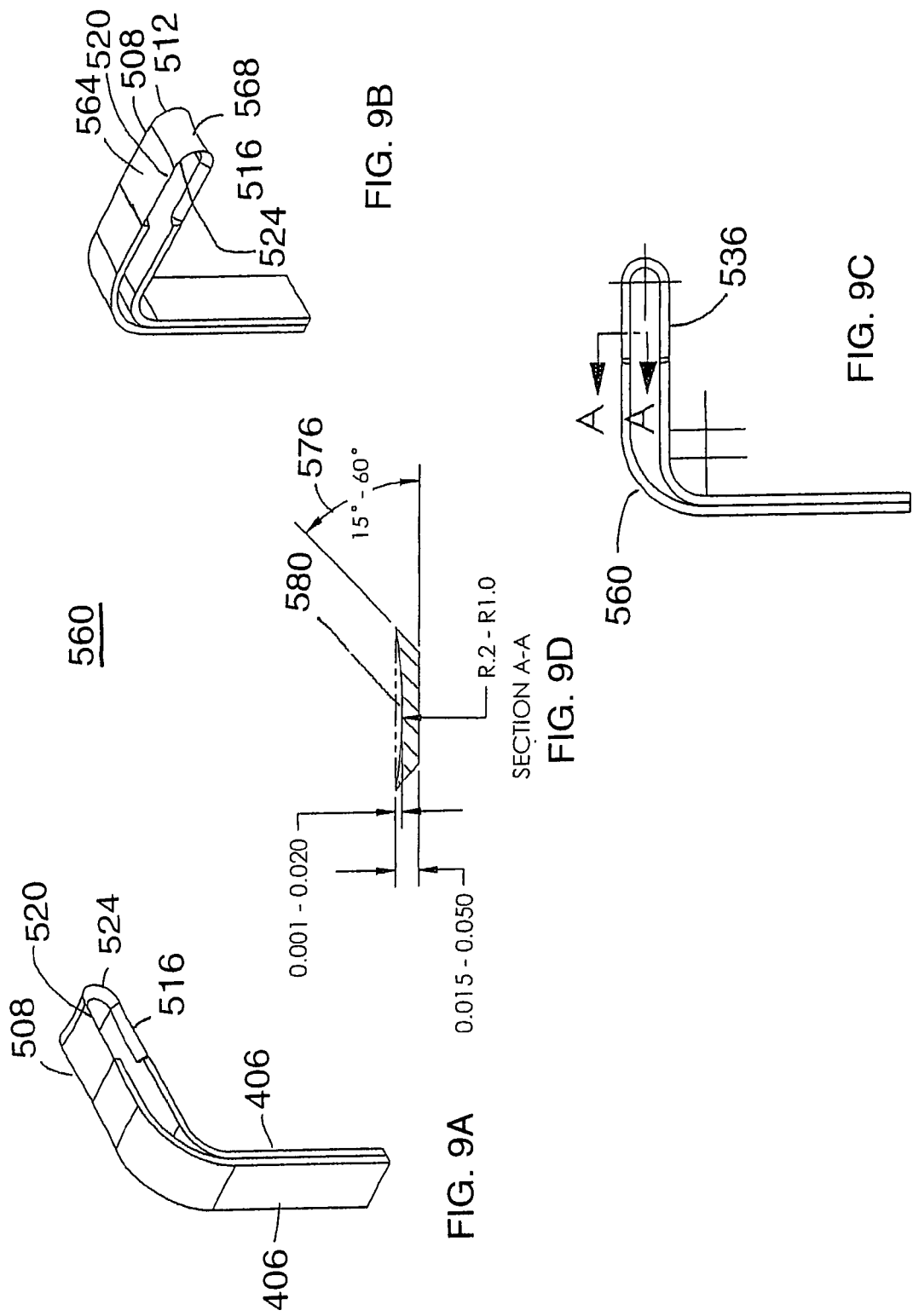
FIGS. 9A-9D show four views of a cutter blade of FIG. 8 with a hollow ground.

FIG. 9D shows a cross section detail A-A of FIG. 9C and shows bevel angle 576 which for some cutter blades may be in the range of 15 to 60 degrees. FIG. 9D also shows that removed material 580 that is removed to make the hollow ground may range in this example from 0.001 inches to 0.020 inches depending in part on the thickness of the blade stock but also the extent to which the hollow ground effect is sought in enhancing the cutting action of the nearby blade edges. To the extent that the surface of the cutter blade is recessed near the blade edges, the blade edges tend to have a more aggressive interaction with material such as cartilage or the endplates of the vertebral bodies. This aggressive interaction tends to promote the efficiency of the cutter blade when scraping/cutting these materials and tends to promote bleeding.

The use of hollow ground to enhance cutter blades may be used with cutter blades using serrated edges in addition to cutter blades such as cutter blade 560 that has a straight beveled edge.

Thin Disc Cutter Blades

Figure 10:
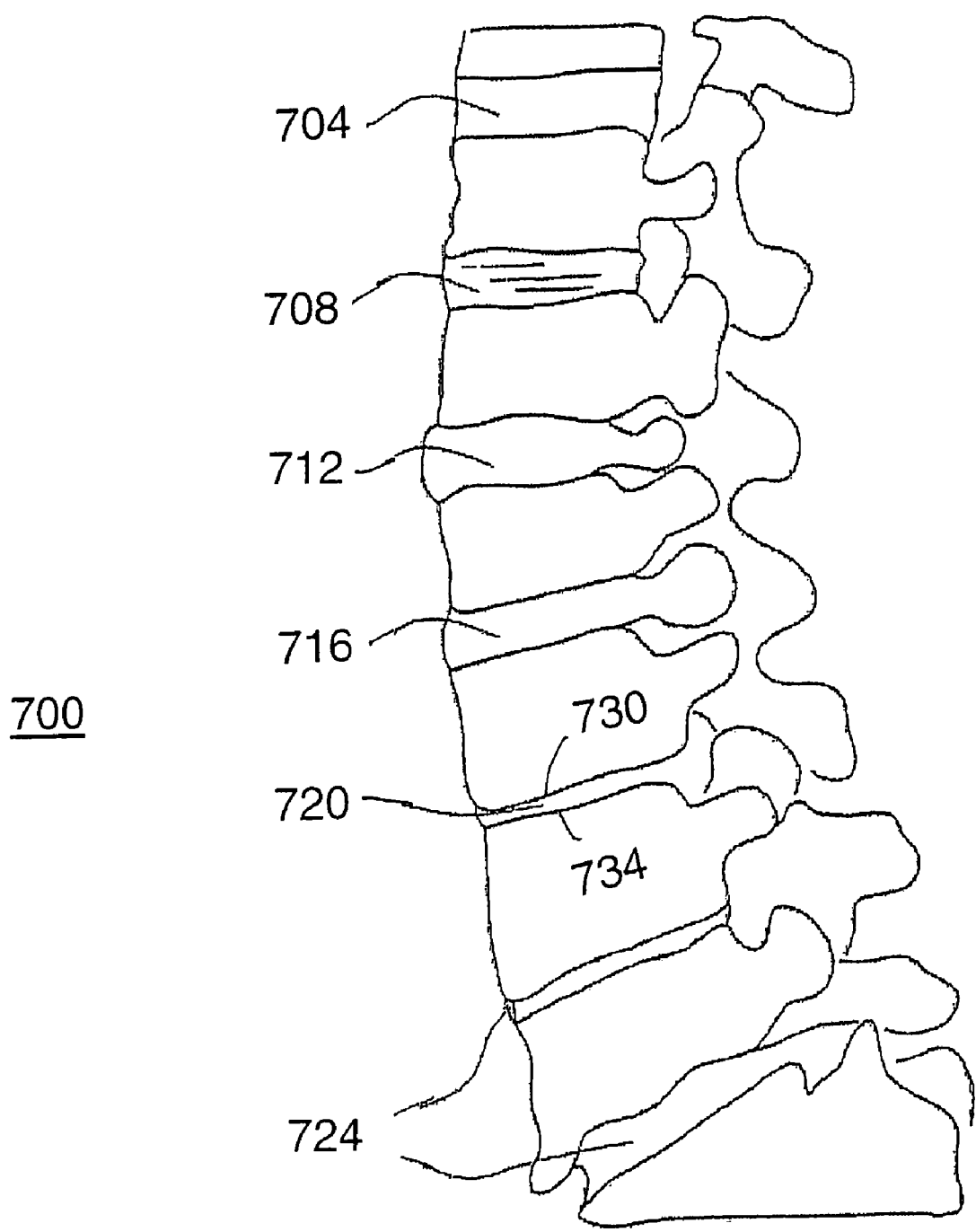
FIG. 10 shows a lateral view of a portion of a human spine.

FIG. 10 shows a lateral view of portion of a human spine 700. Disc 704 illustrates a normal healthy disc. Disc 708 is a deteriorating disc. Disc 712 is a bulging disc. Disc 716 is a herniated disc. Disc 720 is a thinning disc and is noteworthy in that the space between endplates 730 and 734 is greatly reduced in comparison with normal disc 704. Likewise discs 724 which are degenerated discs with osteophyte formations are also thin discs. Closed loop cutter blades such as cutter blade 453 in FIG. 3 and again in FIG. 5 may not be sufficiently thin to operate within a thin disc.

Figure 11:
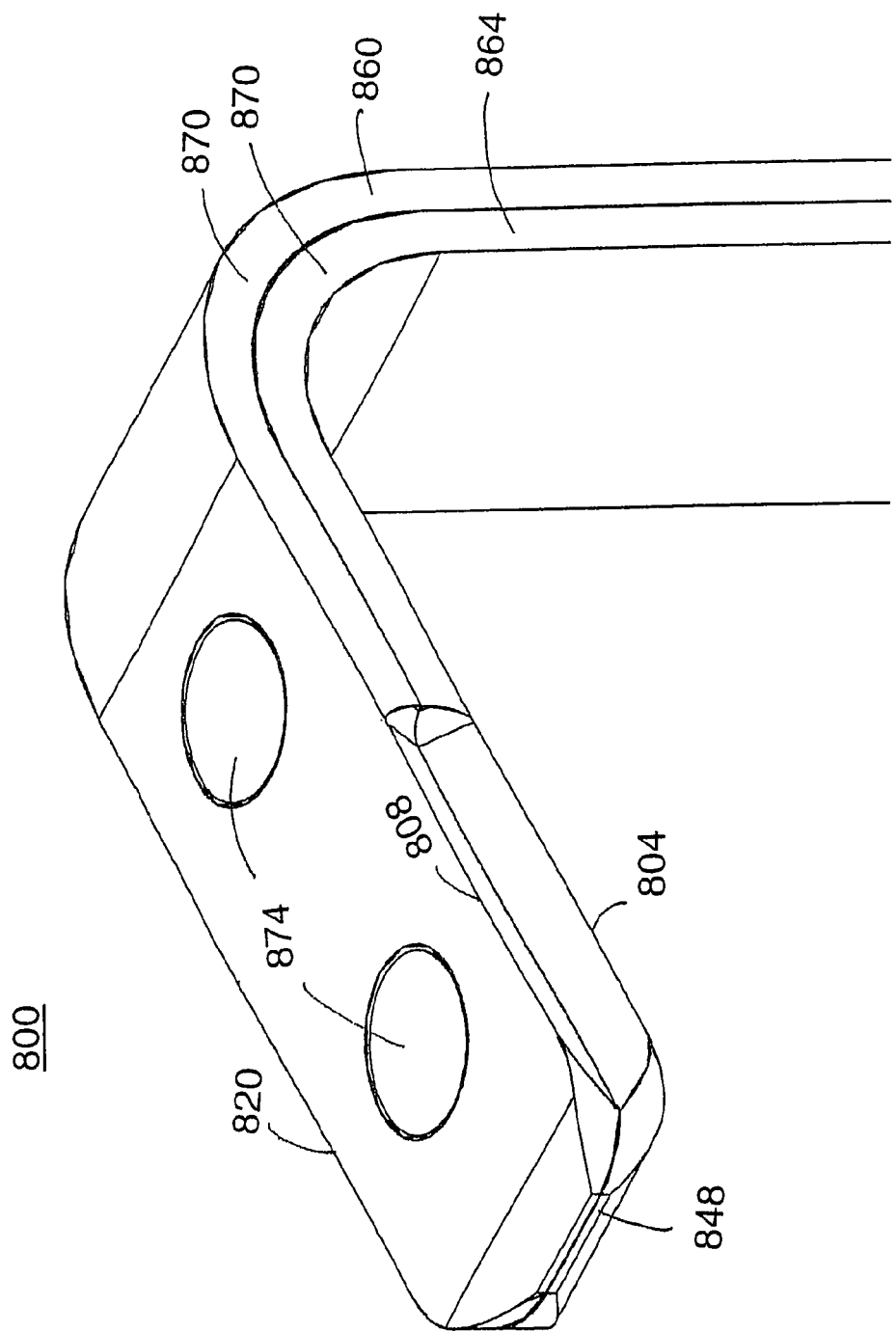
FIG. 11 shows an top perspective view of a thin cutter blade for use in situations such as a thin disc.

FIG. 11 shows an top perspective view of a thin cutter blade 800 for use in situations such as a thin disc. The thin cutter blade 800 has many features that are similar to the cutter blade 500 discussed in connection with FIG. 8. Thin cutter blade 800 has blade edges 808 and 820 on the distal arm 860 and blade edges 804 and 816 (not visible here) on the proximal arm 864.

Unlike the closed loop cutter blade 500, there is not a gap between the distal arm 860 and the proximal arm 864 in the vicinity of the blade edges. Thus the thickness of the cutter blade is on the order of magnitude of only 0.050 inches which is considerably less than found in the closed loop cutter blades such as cutter blade 500 in FIG. 8.

Two rivets 874 are added to retain the flush relationship between the distal arm 860 and the proximal arm 864. After the rivets 874 are pressed, the rivets 874 are made flush with the surface of the distal arm 860 and with the surface of the proximal arm 864 (lower side of rivets not visible in this view). The tip 848 does not have a cutting edge but is rounded or beveled.

Figure 12A:
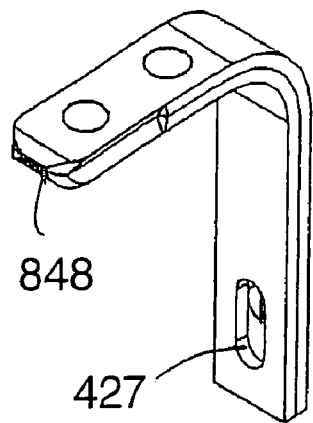
FIGS. 12A-12D provide additional views of the thin cutter blade of FIG. 11.
Figure 12D:
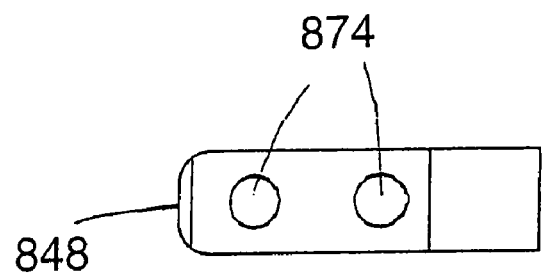
Figure 12B:
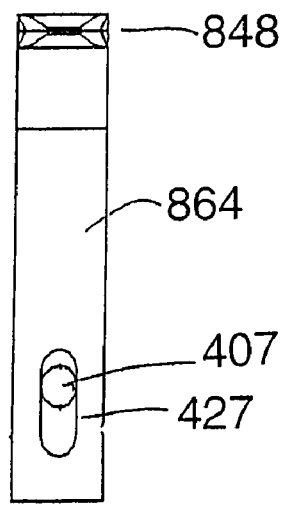
Figure 12C:
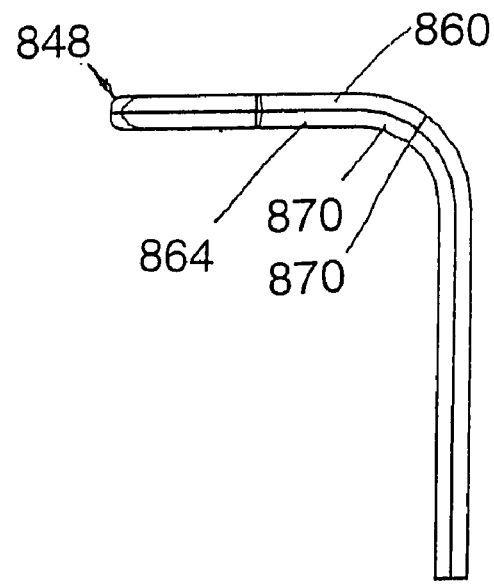

FIGS. 12A-12D provide additional views of thin cutter blade 800. FIG. 12A is a top perspective view of thin cutter blade 800 much like FIG. 11. As FIG. 12A shows the entire thin blade cutter 800 it includes cutter blade slot 427. FIG. 12B, a front view of thin cutter blade 800 shows cutter blade slot 427 that is on the proximal arm 864 and visible through the cutter blade slot 427 is the cutter blade hole 407 that is on distal arm 860. The use of a combination of a slot and a hole allows the proximal arm 864 to move relative to the distal arm 860 as the thin cutter blade 800 is encircled by the cutter sheath and thus constrained to move away from the shape shown in FIG. 12. As the thin cutter blade 800 changes shape, the curvatures in transitional sections 870 changes. FIG. 12C is a side view of thin blade cutter 800 and FIG. 12D is a top view of the thin blade cutter 800

Figure 13:
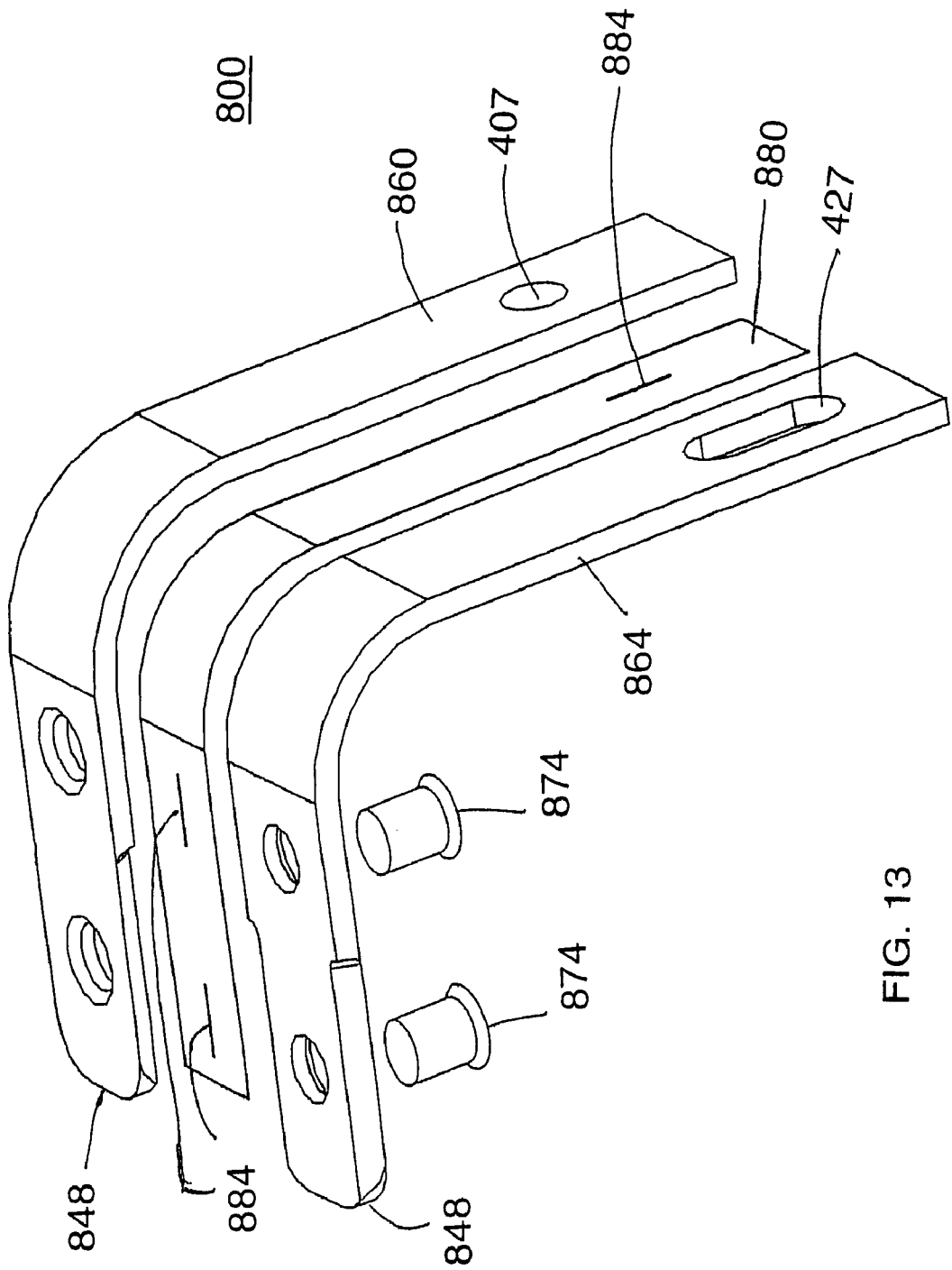
FIG. 13 is a top perspective view of an exploded drawing of thin cutter blade shown in FIG. 11.

FIG. 13 is a top perspective view of an exploded drawing of thin blade cutter 800. Rivets 874 are visible before insertion and pressing. Distal arm 860 and blade cutter hole 407 are visible as are proximal arm 864 and blade cutter slot 427.

Retaining Film

FIG. 13 also shows optional element 880 which is a retaining film. The retaining film 880 is placed between the proximal arm 864 and the distal arm 860 and is affixed to engage each arm. The rivets 874 and the pin or rivet that attaches the thin cutter blade 800 to the cutter shaft pass through slits 884 in the retaining film 880. The retaining film 880 would come into play if the thin cutter blade 880 were to break both the proximal arm 864 and the distal arm 860. The retaining film 880 if operating as intended would not break and would retain the broken section in connection with the rest of the thin cutter blade 800 so that the broken section could be removed from the intervertebral disc space and the axial channel 212 (FIG. 2C).

The retaining film 880 may be made from a high tensile strength, dimensionally stable, biocompatible, sterilizable polymeric film. The retaining film 880 may be made for example from a biaxially-oriented polyethylene terephthalate (boPET) polyester film. In some instances it may be difficult to adequately adhere the retaining film 880 to a shape memory alloy such as Nitinol™. However, as the retaining film 880 is mechanically connected to the distal arm 860 and the proximal arm 864 through the rivets 874 and the connection to the cutter shaft, the retaining film 880 may serve a useful purpose in retaining a broken section of the thin cutter blade 800 unless the break is between the last rivet 874 and the tip 848.

The retaining film 880 may range from between about 0.08 mm to about 0.40 mm in thickness. In addition to retaining broken pieces, the retaining film 880 serves to preclude the shear and or lateral movement of the distal arm 560 relative to the proximal arm 564.

Figure 14A:
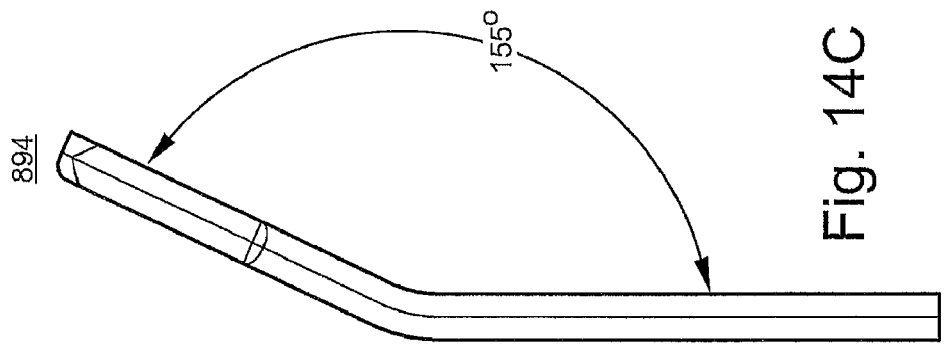
FIG. 14A provides a side view of a thin cutter blade that has a 45 degree angle between the blade arm portion of the proximal arm and the longitudinal portion of the proximal arm.
Figure 14B:
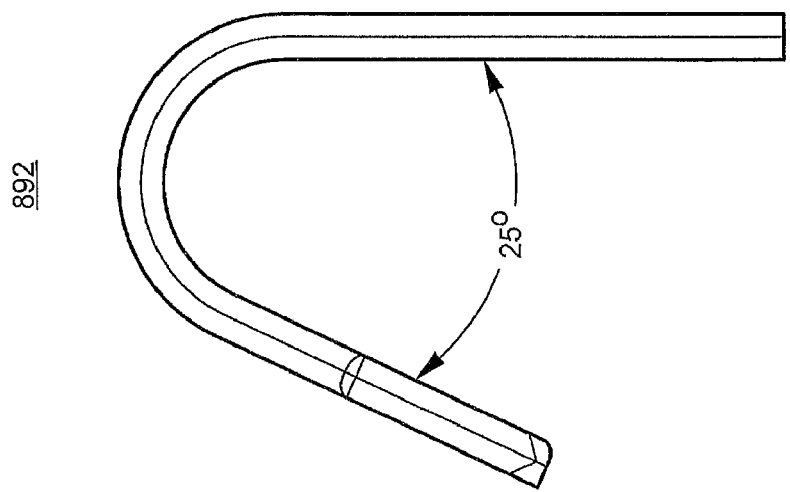
FIG. 14B provides a side view of a thin cutter blade that has a 25 degree angle between the blade arm portion of the proximal arm and the longitudinal portion of the proximal arm.
Figure 14C:
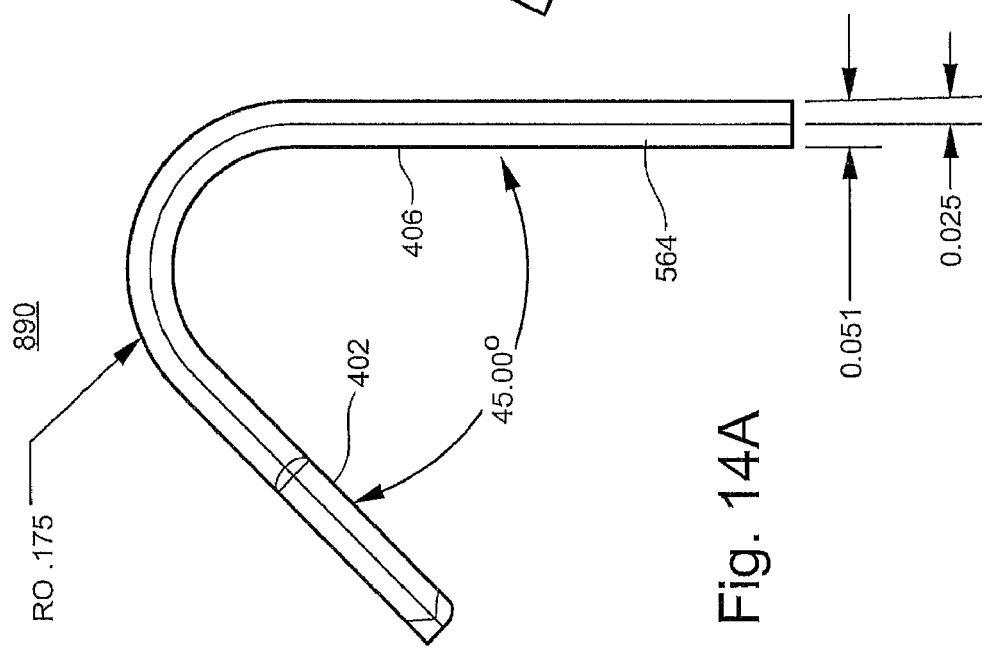
FIG. 14C provides a side view of a thin cutter blade that has a 155 degree angle between the blade arm portion of the proximal arm and the longitudinal portion of the proximal arm.

FIG. 14A provides a side view of a thin cutter blade 890 that has a 45 degree angle between the blade arm 402 portion of the proximal arm 564 and the longitudinal portion 406 of the proximal arm 564. Thin cutter blades with a range of angles may be useful for working in thin discs at the endplates that partially define the intervertebral disc space (see endplates 342 and 352 in FIG. 7) where the endplates are not be substantially perpendicular with the centerline 262 of the cutter assembly as is the case in FIG. 7. The angles may range from 25 to 155 degrees but there may be more demand for angles in the range of 40 to 140 degrees. FIG. 14B provides a side view of a thin cutter blade 892 that has a 25 degree angle. FIG. 14C provides a side view of a thin cutter blade 894 that has a 155 degree angle.

FIG. 15 shows a thin cutter blade 904 with the cutting edges recessed from the exterior surfaces of the thin cutter blade by having adjacent blade edges from the distal arm 560 and the proximal arm 564. While shown with an approximately 90 degree angle, thin cutter blades of this type may be made in a range of angles such as from 30 to 120 degrees.

One of skill in the art will recognize that to the extent that the cutter blades are produced in a finite number of nominal cutter blade angles, the actual measurement of the precise angle may deviate a few degrees (perhaps 5) from the nominal angle value. The actual angle may deviate over cycles of moving from the sheathed to the extended position.

In many situations a set of cutter blades of various combinations of throw lengths and angles (such as 45 degree, 90 degree, and 135 degree) may be sufficient. Some surgeons may feel that they obtain adequate results for some therapies with using just 90 degree and 45 degree cutter blades. Other angles could be used, including angles that deviate less from 90 such as 60 and 120 degrees, or angles that deviate more from 90 degrees such as 25 and 155 degrees. Angles even closer to 90 degrees may be useful in some applications such as an angle in the vicinity of 105 degrees. Kits could include more than three angle values for the cutter blades. For example, a kit might include blades at 25, 45, 60, 90, 105, 120, 135 and 155 degree angles. With this range of blade angles, there is a wide variation of the extent to which the extended blades are transverse to the long axis of the cutter assembly, but in all these cases the cutter blades are significantly transverse to the long axis of the cutter assembly and to the longitudinal portions of the cutter blades.

Some surgeons may work by initially using a short 90 degree cutter blade, then using progressively longer 90 degree cutter blades (one or more longer cutter blades) to cut as much material within the intervertebral disc space 312 as can be safely handled using 90 degree cutter blades. Then the surgeon may want to work with a short 45 degree cutter blade then one or more longer 45 degree cutter blades to remove material that would be difficult to access using a 90 degree cutter blade. Finally, in some cases, the surgeon may opt to use a short 135 degree cutter blade followed by one or more longer 135 degree cutter blades to cut nucleus material that is difficult to access using either a 90 degree or a 45 degree cutter blade.

FIG. 16 shows an "L" cutter blade 910 which used a single arm rather than a pair of arms (560 and 564 as in FIG. 15). The "L" cutter blade 910 shown in FIG. 16 has a pair of cutting edges 914 and 918 on the distal surface 922 of the "L" blade 910. The blade edge may be cut at a bevel angle of approximately 25 to 80 degrees as indicated in FIG. 16D. The "L" cutter blade 910 of FIG. 16 may be used to scrape the cartilage and endplate on the distal endplate 730 (See FIG. 10). The advantage of a "L" cutter blade such as 910 over a thin cutter blade such as 800 shown in FIG. 11 is that the height of the "L" cutter blade is approximately half that of the thin cutter blade 800 as the "L" cutter blade effectively uses one arm instead of a stack of two (a proximal arm and a distal arm). Thus an "L" cutter blade may be able to work in a thin disc that is too thin for even a thin cutter blade.

FIG. 17 shows a number of views of an "L" cutter blade 930 that is much like "L" cutter blade 910 except that the cutting edges 934 and 938 are on the proximal side of the "L" cutter blade 930. The "L" cutter blade 930 may be used to scrape the endplate 734 on the more proximal vertebral body (assumes a trans-axial approach as shown in FIG. 2). The bevel angles and range of cutter blade angles for "L" cutter blade 930 may be the same as for "L" cutter blade 910.

Figure 19:
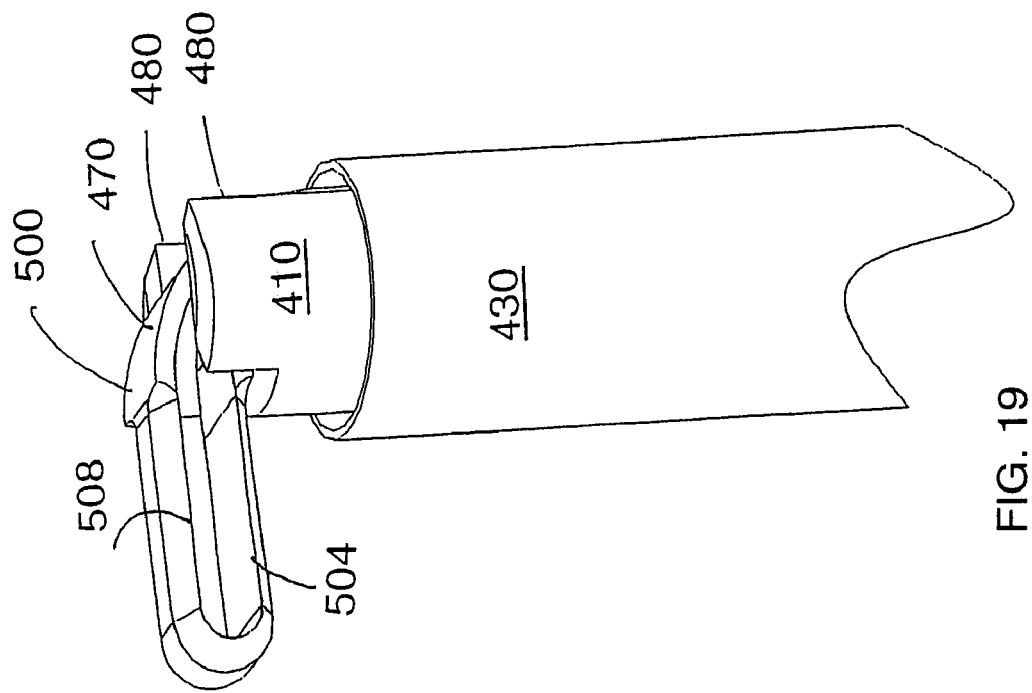
FIGS. 18-19 focus on cutter shafts and the use of cutter shaft extensions.
Figure 18:
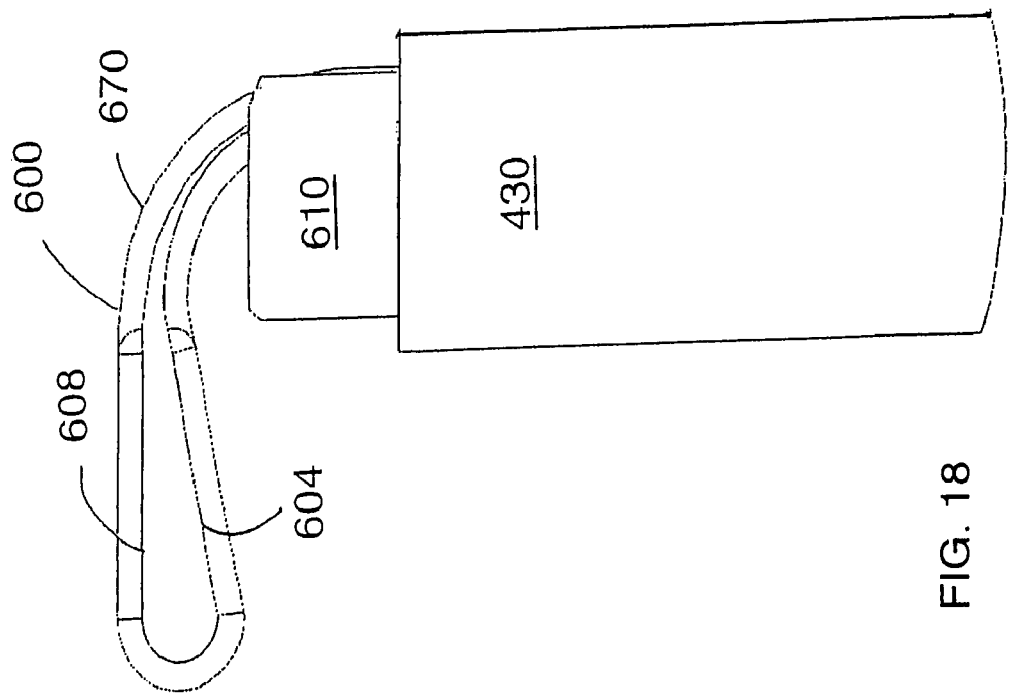

FIGS. 18 and 19 allow a discussion of a feature in cutter shaft 410 that was visible in FIGS. 5A and 5B. Cutter shaft 610 receives the longitudinal portion of cutter blade 600 into a slot and the cutter blade 600 may be pinned to cutter shaft 610 in the manner discussed with respect to FIGS. 5A and 5B. However, the cutter shaft 610 differs from cutter shaft 410 in that it lacks the cutter shaft extensions 480. These cutter shaft extensions 480 (sometimes called goal posts) provide additional support to the cutter blade 500. This additional support may be desired, in particular, for cutter blades with longer throws.

When seeking to create cutter assemblies for use with thin cutter blades or "L" cutter blades, it may be desirable to use cutter shafts without cutter shaft extension 480 in order to minimize the height of the cutter shaft in addition to controlling the height of the cutter blade.

A second reason for using a cutter shaft 610 without cutter shaft extensions 480 is when using a short throw cutter blade with a desire to allow more flex in the blade. In some instances, additional flex in the shorter throw cutter blades is thought to help, the cutter blade cut more effectively.

FIG. 20 is the distal end of a cutter shaft such as cutter shaft 610. FIG. 21 is an enlarged detail of FIG. 20. FIG. 22 is a cross section of the distal end of cutter shaft 610. Analogous drawings for a cutter shaft 410 with cutter shaft extensions 480 are shown in FIGS. 23-25.

Material Choices and Other Details

In the context of the present invention, the term "biocompatible" refers to an absence of chronic inflammation response or cytotoxicity when or if physiological tissues are in contact with, or exposed to (e.g., wear debris) the materials and devices of the present invention. In addition to biocompatibility, in another aspect of the present invention it is preferred that the materials comprising the instruments are sterilizable; visible and/or imaginable, e.g., fluoroscopically.

The cutter shaft and cutter sheath are typically fabricated from a metal or metal alloy, e.g., stainless steel and can be either machined or injection molded.

Due to limited disc height in certain patients, e.g., where fusion is indicated due to herniated or collapsed discs, cutter blades are preferably constructed to have a lower profile during extension, use, and retraction.

In one aspect of the present invention, the separation distance between the first and second cutting edges is a controllable variable in manufacturing (that is, predetermined during cutter blade formation, through heat treatment of the pinned, preferred nickel-titanium shape-memory alloy, e.g., Nitinol™). The separation distance between cutting edges varies from about 2 mm to about 8 mm, and, often is about 3 mm to about 4 mm. Some cutter blades have a tear drop shape. The maximum separation between cutting edges may be located within about the radially outwardly most one third of the total blade length. Alternatively, the maximum separation may be positioned within the radially inwardly most third of the blade length, or within a central region of the blade length, depending upon the desired deployment and cutting characteristics.

In accordance with one aspect of the embodiments described herein, the blade arms and the cutter blades in general can be formed from strip material that is preferably a shape memory alloy in its super-elastic or austenitic phase at room and body temperature and that ranges in width from about 0.10 inches (2.5 mm) to about 0.20 inches (5 mm) and in thickness from about 0.015 inches (0.38 mm) to about 0.050 inches (1.3 mm). Blade arms formed in accordance with the present embodiment are generally able to be flexed in excess of 100 cycles without significant shape loss, and twisted up to one and ½ full turns (about 540 degrees) without breakage. This is twisting of one end of the cutter blade relative to another portion of the cutter blade.

The shape memory feature is useful both in allowing the cutter blade to resume the extended position which is in shape memory but the shape memory helps the cutter blade resume its intended shape after being distorted while being rotated within the intervertebral disc space and receiving uneven resistance to motion.

In one embodiment, the cutting blade and cutter blade edge is formed from a super-elastic, shape memory metal alloy that preferably exhibits biocompatibility and substantial shape recovery when strained to 12%. One known suitable material that approximates the preferred biomechanical specifications for cutter blades and cutter blade edges and blade arms is an alloy of nickel and titanium (e.g., $Ni_{56}$—$Ti_{45}$ and other alloying elements, by weight), such as, for example, Nitinol strip material #SE508, available from Nitinol Devices and Components, Inc. in Fremont, Calif. This material exhibits substantially full shape recovery (i.e., recovered elongation when strained from about 6%-10%, which is substantially better than the recovered elongation at these strain levels of stainless steel).

The shape and length of the formed cutter blade in general varies for the different cutting modes. The shape memory material can be formed into the desired cutter blade configuration by means of pinning alloy material to a special forming fixture, followed by a heat-set, time-temperature process, as follows: placing the Nitinol strip (with the blade's cutting edge(s) already ground) into the forming fixture and secured with bolts; and placing the entire fixture into the oven at a temperature ranging from about 500° C. to about 550° C. (e.g., where optimum temperature for one fixture is about 525° C.) for a time ranging from between about 15 to about 40 minutes (e.g., where the optimum time for one fixture is about 20 minutes). Flexible cutter blades formed from Nitinol in this manner are particularly suited for retraction into a shaft sleeve, and are able to be extended to a right angle into the disc space. Moreover, they are able to mechanically withstand a large number of cutting "cycles" before failure would occur.

The cutting blade edges are preferably ground with accuracy and reproducibly. The angle of the inclined surface of the blade relative to the blade's flat side surface typically ranges from about 5 degrees to about 70 degrees, often about 20 degrees to about 50 degrees. In one embodiment, the blade angle is approximately 30 degrees relative to the blade's side surface.

In one aspect of the present invention, cutter blades configured with serrations are formed by a wire EDM (Electrical Discharge Machining) process to optimize design profiles. For higher manufacturing volumes, cutter blades are formed via profile grinding; progressive die stamping; machining, or conventional EDM.

In one embodiment, the shaft of the assembly is formed from solid stainless steel or other known suitable material. In one embodiment, the shaft has a diameter of approximately 0.25 inches (6.3 mm). The cutter shaft sheath may be formed from stainless steel rod or bar or other known suitable material tubing, and has a length of about 0.7 inches (17.8 mm).

As will be understood by one of skill in the art, certain components or sub-assemblies of the assemblies of the present invention may alternatively be fabricated from suitable (e.g., biocompatible; sterilizable) polymeric materials, and, for example, may be coated (e.g., with PTFE) to reduce friction, where appropriate or necessary.

For example, the cutter sheath can be fabricated from polymeric material, stainless steel, or a combination of stainless steel tubing with a low friction polymeric sleeve such as UHMWPE, HDPE, PVDF, PTFE loaded polymer. The sheath typically has an outer diameter (O.D.) of about 0.31 inches (7 mm) to about 0.35 inches (9 mm).

Alternatives

Alternative method of affixing the blade to the blade shaft.

Figure 26A:
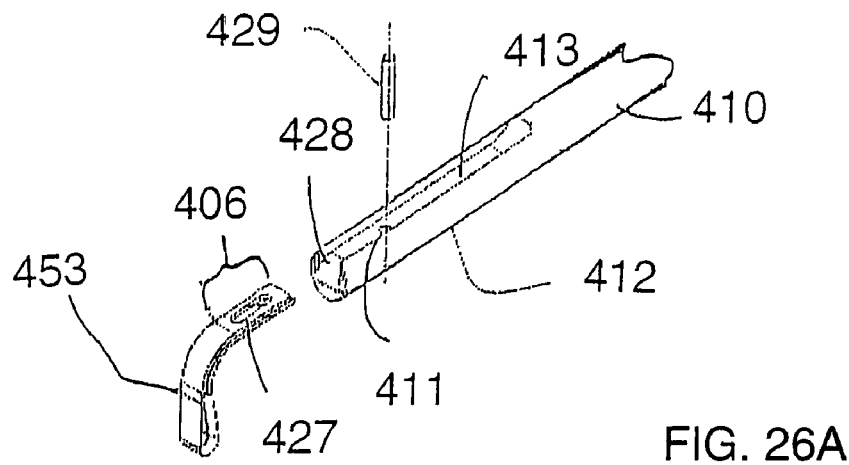
FIGS. 26A-26B are a cutter blade attached to a cutter shaft by a rivet.
Figure 26B:
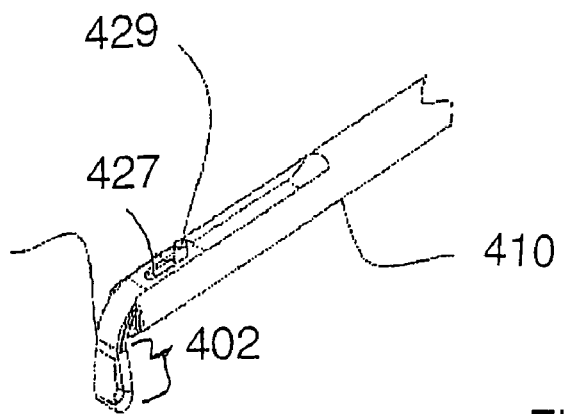
Figure 26C:
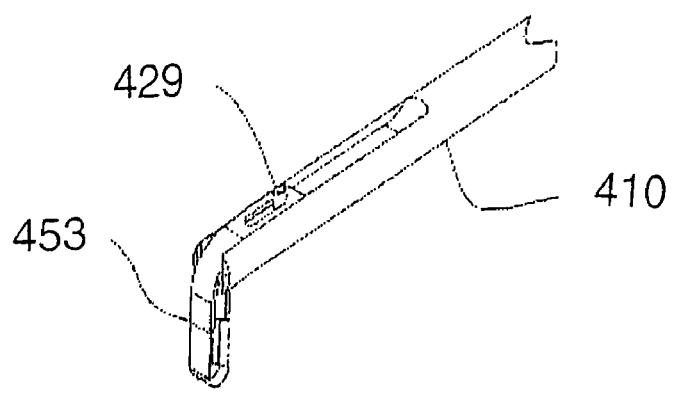
FIG. 26C shows a cutter blade attached to a cutter shaft with a rivet where the cutter shaft has cutter shaft extensions.

In FIGS. 26A-26B, a cutter blade 453 is placed in a shaft slot 413 in a distal end 412 of a cutter shaft 410 by a rivet 429 that passes through a cutter blade slot 427 and the cutter blade hole (407 but not visible here) and into a cutter shaft hole 411. When using a rivet, a shaft sleeve (compare element 418 in FIGS. 5A and 5B) is not required. FIG. 26C shows that this method of fixation can be combined with the goal post feature described above.

While the certain cutter blades disclosed above have used a cutter blade hole 407 on the proximal arm and a cutter blade slot 427 on the distal arm, one of skill in the art will appreciate that one could modify the cutter blades and the cutter shaft to allow the use of the cutter blade hole on the distal arm and the cutter blade slot on the proximal arm without deviating from the spirit of the teachings of the present disclosure. Likewise, examples showing the cutter blade hole on the distal arm and the cutter blade slot on the proximal arm could be modified to swap the hole and the slot.

Likewise, one could modify the cutter blades shown above to allow for at least some types of cutter blades with holes on both longitudinal portions so that once pinned there was not relative motion of one longitudinal portion relative to the other. Other non-pin attachment choices could be used that would not allow relative movement. This alternative would rely more on the ability of the shape memory material to resume a given shape as the pinned longitudinal portions could not move relative to one another to help with the transformation.

Cutter shafts may be specialized to work with specific cutter blades with specific blade angles. For example, it may be advantageous to use a cutter shaft for a 45 degree blade that allows the 45 degree blade to begin its downward angle while still in contact with the cutter shaft. Alternatively, a standard cutter shaft could be used for a range of cutter blade angles and the variation in blade angles would be handled in the cutter blades after the cutter blade has left contact with the cutter shaft. A combination of both strategies might call for a few different cutter shafts such as a 45 degree cutter shaft and a 90 degree cutter shaft and using attributes of the cutter blades to provide an expanded range of cutter blade angles.

The cutter assemblies described herein may also be used in conjunction with other methods, such as hydro-excision or laser to name just two examples to perform partial or complete nucleectomies, or to facilitate other tissue manipulation (e.g., fragmentation and/or extraction).

Alternative Handle

In accordance with one aspect of the embodiments described herein, there is provided a handle configured, for example, as a lever or pistol grip, which is affixed to the proximal end of the cutter shaft. Referring to FIG. 4B, the illustrated handle 416 is affixed to the proximal end 414 of the cutter shaft 410 by a cross-pin or set screw, which reduces the risk of handle disengagement from the cutter shaft 410 (unthreading by rotational manipulation during cutting). As mentioned, the handle 416 is preferably affixed so that it is in rotational positional alignment with the blade arm and serves as a reference marker for the blade arm's in situ orientation.

Alternatively, the handle of the cutter assembly is configured as a turn knob (not shown) fabricated from a polymeric material, such as, for example, ABS polymer or the like, that is injection moldable and that may be machined, and is affixed to the cutter shaft by means of threaded or other engagement to the cutter shaft proximal end.

Rotational Stops

In accordance with one aspect of the embodiments described herein, there are provided blade arms and cutters that are designed to be rotated and used in one direction (i.e., clockwise or counter-clockwise), i.e., the rotational motion of blade arms in only one direction (e.g., clockwise) will initiate severing of nucleus material The intended motion during the use of these blades is similar to the back and forth motion of a windshield wiper—wherein the excision with respect to these cutters occurs in the sweep that is clockwise in direction.

In one embodiment (not shown), one or more stops are placed within the cutter shaft to control blade arc or range of motion. In another embodiment (not shown), one or more stops are fitted onto the cutter sheath to control the blade arc or range of motion.

Kits

Various combinations of the tools and devices described above may be provided in the form of kits, so that all of the tools desirable for performing a particular procedure will be available in a single package. Kits in accordance with the present invention may include preparation kits for the desired treatment zone, i.e., provided with the tools necessary for disc preparation. Disc preparation kits may differ, depending upon whether the procedure is intended to be in preparation for therapy of one or more vertebral levels or motion segments. The disc preparation kit may include a plurality of cutters. In a single level kit, anywhere from 3 to 7 cutters and, in one embodiment, 5 cutters are provided. In a two level kit, anywhere from 5 to 14 cutters may be provided, and, in one embodiment, 10 cutters are provided. The cutter assemblies will include an assortment of cutter blades. The assortment will be different depending on the specific procedure to be performed and possibly based on the patient anatomy (which may impact the range of cutter blade throw lengths needed).

Typically, a kit will include cutter assemblies with a small radial cutter blade, a medium radial cutter blade, and a large radial cutter blade. The kit will typically also include three more cutter assemblies with small, medium, and large cutter blades with a blade angle of 45 degrees. Kits for specific procedures may include other cutter assemblies with specific cutter blades for specific uses for example inclusion of cutter blades chosen for there ability to cut into and cause bleeding in either the inferior or superior endplates. All of the cutters blades are one-time use, i.e., disposable. Certain other components comprised within the cutter assembly may be disposable or reusable.

The disc preparation kit may (optionally) additionally include one or more tissue extraction tools, for removing fragments of the nucleus. In a one level kit, 3 to 8 tissue extraction tools, and, in one embodiment, 6 tissue extraction tools are provided. In a two level disc preparation kit, anywhere from about to 8 to about 14 tissue extraction tools, and, in one embodiment, 12 tissue extraction tools are provided. The tissue extraction tools may be disposable.

The two arm thin cutter blades shown above include two rivet connections in the blade arm. One of skill in the art will appreciate that a single rivet or more than two rivets could be used. Likewise, other mechanical connections could be substituted for rivets.

The cutters described above have been described in the context of use within an intervertebral disc space. One of skill in the art will recognize that the desirable attributes of the disclosed cutters could be used within other medical procedures that access material to be cut (most likely for removal before a subsequent therapeutic procedure) by delivery of a cutter blade in a sheathed state to through a lumen before the cutter blade assumes an extended position in which the cutter blade has as a shape memory. One of skill in the art will recognize that the dimensions of the cutter blade and related components may need to be adjusted to meet the relevant anatomic dimensions and the dimension of the lumen used for providing access. While there may not be cartilage covered vertebral body endplates to preserve or scrape (depending on the desired results) there may be other anatomic structures that need to be protected from cutting edges or alternatively need to be scraped as part of site preparation, thus making many of the specific teachings of the present disclosure relevant.

One of skill in the art will recognize that some of the alternative implementations set forth above are not universally mutually exclusive and that in some cases additional implementations can be created that employ aspects of two or more of the variations described above. For example the hollow ground treatment for enhancing the cutting ability of a blade edge while shown in connection with a closed loop cutter blade could be used in connection with a thin cutter blade. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

What is claimed is:

1. A thin cutter blade for use in an intervertebral disc space, the cutter blade created at least in part from a shape memory material and having a shape memory of a shape that the cutter blade assumes when not constrained from doing so and the cutter blade comprising:
   a proximal arm with a first longitudinal portion with a first cutter blade connection for use in affixing the proximal arm to a cutter assembly, the proximal arm also having a blade arm portion with at least one cutting edge;
   a distal arm, distinct from the proximal arm with a second longitudinal portion with a second cutter blade connection for use in connecting the second longitudinal portion to the cutter assembly, the proximal arm also having a blade arm portion with at least one cutting edge;
   a layer of retaining film positioned between the distal arm and the proximal arm and affixed to both the distal arm and the proximal arm; and
   a connection between the blade arm portion of the proximal arm and the blade arm portion of the distal arm.

2. The thin cutter blade of claim 1 wherein:
   the proximal arm also having a blade arm portion with at least one cutting edge on an external surface of the proximal arm that is the surface on the opposite side from a distal arm; and
   the proximal arm also having a blade arm portion with at least one cutting edge on an external surface of the distal arm, that is the surface on the opposite side from the proximal arm.

3. The thin cutter blade of claim 2 wherein the first cutter blade connection is a slot.

4. The thin cutter blade of claim 2 wherein the second cutter blade connection is a slot.

5. The thin cutter blade of claim 2 wherein the connection between the blade arm portions is a rivet.

6. The thin cutter blade of claim 2 wherein the connection between the blade arm portions is at least two rivets.

7. The thin cutter blade of claim 2 wherein the distal arm has a second cutting edge on the external surface of the distal arm, such that the distal arm is adapted to be connected to a cutter shaft and when the extended cutter blade is rotated around the centerline of a long axis of the cutter shaft the distal arm has a cutting edge for use with clockwise rotation and a cutting edge for use with counterclockwise rotation.

8. The thin cutter blade of claim 2 wherein the proximal arm has a second cutting edge on the external surface of the proximal arm, such that the proximal arm is adapted to be connected to a cutter shaft and when the extended cutter blade is rotated around the centerline of a long axis of the cutter shaft the proximal arm has at least one cutting edge for use with clockwise rotation and at least one cutting edge for use with counterclockwise rotation.

9. The thin cutter blade of claim 2 wherein the angle between the proximal arm blade arm portion and the proximal arm longitudinal portion is in the range of about 25 to about 155 degrees.

10. The thin cutter blade of claim 2 wherein the angle between the proximal arm blade arm portion and the proximal arm longitudinal portion is in the range of about 25 to about 90 degrees.

11. The thin cutter blade of claim 2 wherein the angle between the proximal arm blade arm portion and the proximal arm longitudinal portion is in the range of about 90 to about 155 degrees.

12. The thin cutter blade of claim 1 wherein the retaining film is adhered to both the distal arm and the proximal arm.

13. The thin cutter blade of claim 12 wherein connections between the proximal arm and the distal arm pass through the retaining film and the retaining film has an opening aligned with the first cutter blade connection and the second cutter blade connection.

14. The thin cutter blade of claim 1 wherein the distal arm has a cutting edge recessed from an external surface of the distal arm, that is the surface on the opposite side from the proximal arm.

15. The thin cutter blade of claim 1 wherein the proximal arm has a cutting edge recessed from an external surface of the proximal arm, that is the surface on the opposite side from the distal arm.

16. The thin cutter blade of claim 1 wherein the connection between the blade arm portion of the proximal arm and the blade arm portion of the distal arm maintains the blade arm portion of the proximal arm in sufficient proximity with the blade arm portion of the distal arm such that thin cutter blade does not have an opening between the blade arm portion of the proximal arm and the blade arm portion of the distal arm sufficient to allow intervertebral disc space material to pass through the opening as the thin cutter blade is rotated in the intervertebral disc space.

17. The thin cutter blade of claim 1 wherein a thickness of the thin cutter blade as measured from the external surface of the proximal arm along the blade arm portion to the external surface of the distal arm along the blade arm portion is between about 0.030 inches to about 0.116 inches.

* * * * *

UNITED STATES PATENT AND TRADEMARK OFFICE
CERTIFICATE OF CORRECTION

PATENT NO. : 7,632,274 B2  Page 1 of 1
APPLICATION NO. : 11/712241
DATED : December 15, 2009
INVENTOR(S) : Assell et al.

It is certified that error appears in the above-identified patent and that said Letters Patent is hereby corrected as shown below:

On the Title Page, item (60), an additional heading entitled --Related U.S. Application Data-- should be inserted below the heading entitled "Prior Publication Data." Under the heading entitled "Related U.S. Application Data," the following application should be listed: --Provisional application No. 60/778,035, filed on Feb. 28, 2006.--

Signed and Sealed this

Sixth Day of July, 2010

David J. Kappos
*Director of the United States Patent and Trademark Office*

UNITED STATES PATENT AND TRADEMARK OFFICE
CERTIFICATE OF CORRECTION

PATENT NO. : 7,632,274 B2  Page 1 of 1
APPLICATION NO. : 11/712241
DATED : December 15, 2009
INVENTOR(S) : Assell et al.

It is certified that error appears in the above-identified patent and that said Letters Patent is hereby corrected as shown below:

On the Title page:

References Cited, U.S. Patent Documents, Patent No. 1,388,547, "Bums" should be changed to "Burns".

In the Claims:

Column 21, Line 25, Claim 1 "the proximal arm also having" should be changed to "the distal arm also having".

Column 21, Line 33, Claim 2 "a blade arm portion" should be changed to "the blade arm portion.".

Column 21, Line 36, Claim 2 "a distal arm" should be changed to "the distal arm".

Column 21, Line 37, Claim 2 "the proximal arm also having a blade arm portion" should be changed to "the distal arm also having the blade arm portion".

Column 21, Line 52, Claim 7 "the extended cutter blade" should be changed to "an extended cutter blade".

Column 22, Line 6, Claim 8 "the extended cutter blade" should be changed to "an extended cutter blade".

Column 22, Line 42, Claim 16 "such that thin cutter blade" should be changed to "such that the thin cutter blade".

Column 22, Line 49, Claim 17 "the external surface" should be changed to "an external surface".

Column 22, Line 50, Claim 17 "the external" should be changed to "an external".

Signed and Sealed this

Seventh Day of December, 2010

David J. Kappos
*Director of the United States Patent and Trademark Office*